United States Patent
Youn et al.

(10) Patent No.: US 10,744,114 B2
(45) Date of Patent: Aug. 18, 2020

(54) USE OF EUPATILIN AS PHARMACEUTICAL COMPOSITION FOR PREVENTION AND TREATMENT OF FIBROSIS USING EMT INHIBITORY ACTIVITY

(71) Applicant: OSTEONEUROGEN INC., Seongnam-si, Gyeonggi-do (KR)

(72) Inventors: Byung Soo Youn, Seoul (KR); Han Soo Kim, Seoul (KR); Ho Sup Yoon, Nanyang (SG)

(73) Assignee: OSTEONEUROGEN INC., Seongnam-si, Gyeonggi-do (KR)

( * ) Notice: Subject to any disclaimer, the term of this patent is extended or adjusted under 35 U.S.C. 154(b) by 0 days.

(21) Appl. No.: 16/378,590

(22) Filed: Apr. 9, 2019

(65) Prior Publication Data

US 2019/0231739 A1    Aug. 1, 2019

Related U.S. Application Data

(63) Continuation of application No. 15/347,795, filed on Nov. 10, 2016.

(30) Foreign Application Priority Data

| Feb. 22, 2016 | (KR) | 10-2016-0020673 |
| Mar. 18, 2016 | (KR) | 10-2016-0032719 |
| May 23, 2016 | (KR) | 10-2016-0062556 |
| Sep. 13, 2016 | (KR) | 10-2016-0118158 |

(51) Int. Cl.
*A61K 31/35*  (2006.01)
*A61K 31/353*  (2006.01)

(52) U.S. Cl.
CPC .................... *A61K 31/353* (2013.01)

(58) Field of Classification Search
CPC ...................................... A61K 31/352
USPC ............................................. 514/456
See application file for complete search history.

(56) References Cited

U.S. PATENT DOCUMENTS

| 6,555,523 B1 | 4/2003 | Prendergast |
| 2005/0049206 A1 | 3/2005 | Gong et al. |
| 2011/0171193 A1 | 7/2011 | Zhao |
| 2016/0015709 A1 | 1/2016 | Cheresh et al. |

FOREIGN PATENT DOCUMENTS

| CN | 101455718 A | 6/2009 |
| CN | 103655544 A | 3/2014 |
| CN | 103655545 A | 3/2014 |
| CN | 103655546 A | 3/2014 |
| CN | 105663115 A | 6/2016 |

(Continued)

OTHER PUBLICATIONS

Vinken "Gap junctions and non-neoplastic liver diseases," J. Hepatology, 2012, vol. 57, pp. 655-662. (Year: 2012).*

(Continued)

*Primary Examiner* — Shengjun Wang
(74) *Attorney, Agent, or Firm* — Revolution IP, PLLC

(57) ABSTRACT

A pharmaceutical composition contains the chromone derivative of Chemical Formula 1 and a pharmaceutically acceptable salt as an active ingredient, thus effectively inhibiting the activation of EMT to thereby enable the effective suppression of a disease caused by fibrosis of an organ or tissue in vivo due to the activation of EMT.

1 Claim, 15 Drawing Sheets

(56) References Cited

FOREIGN PATENT DOCUMENTS

| KR | 20060121997 | * | 11/2006 |
|---|---|---|---|
| KR | 10-0705199 B1 | | 4/2007 |
| KR | 10-1127158 B1 | | 3/2012 |
| KR | 10-1184725 B1 | | 9/2012 |
| KR | 10-1467109 B1 | | 12/2014 |
| WO | 2009/152453 A2 | | 12/2009 |
| WO | 2010/038153 A1 | | 4/2010 |

OTHER PUBLICATIONS

Park et al. "Eupatilin attenuates bile acid-induced hepatocyte apoptosis," J. Gastroenterol, 2006: vol. 41, pp. 772-778. (Year: 2006).*
Grande MT et al., Snail1-induced partial epithelial-to-mesenchymal transition drives renal fibrosis in mice and can be targeted to reverse established disease. Nat Med., Sep. 2015; 21(9):989-97.
Lovisa S et al., Epithelial-to-mesenchymal transition induces cell cycle arrest and parenchymal damage in renal fibrosis., Nat Med. Sep. 2015;21 (9):998-1009.
Suzuki M et al., the basic helix-loop-helix (bHLH) transcription factor DEC2 negatively regulates Twist1 through an E-box element., Biochem Biophys Res Commun. Dec. 12, 2014;455(3-4):390-5.
Sato F et al., The basic helix-loop-helix transcription factor DEC2 inhibits TGF-β-induced tumor progression in human pancreatic cancer BxPC-3 cells., Int J Mol Med. Sep. 2012; 30(3):495-501.
Dong Y et al., Blocking follistatin-like 1 attenuates bleomycin-induced pulmonary fibrosis in mice., J Exp Med. Feb. 9, 2015; 212 (2):235-52.
Hong-Jhang Chen et al., "Scutellariae radix suppresses LPS-induced liver endothelial cell activation and inhibits hepatic stellate cell migration", Journal of Ethnopharmacology 150 (2013) 835-842.
Cao, Huan-Huan et al., "Polymethoxylated flavonoids activate cystic fibrosis transmembrane conductance regulator chloride channel", Acta Physiologica Sinica, Apr. 25, 2015, 67(2): 225-234.
Lee, S. et al., Food and Chemical Toxicology 46, (2008), 2865-2870.
Calvin et al., "Anti-inflammatory activity of Flavonoids from Eupatorium arnottianum" J. Ethnopharmacology, 2007, vol. 112, pp. 585-589. (Year: 2007).
Jae Youn Cheong et al., "Suppressive Effects of Antioxidant DA-9601 on Hepatic Fibrosis in Rats", Korean J. Hepatol., 2002, vol. 8, p. 436-447.
Eun-Ju Choi et al., "Eupatifin Protects Gastric Epithelial Cells from Oxidative Damage and Down-Regulates Genes Responsible for the Cellular Oxidative Stress", Pharmaceutical Research, vol. 25, No. 6, Jun. 2008.
Hye Young Ji et al., "Metabolism of eupatilin in rats using liquid chromatography/electrospray mass spectrometry", Biomedical Chromatography. Apr. 2004;18(3):173-177.
Piche et al., "The severity of liver fibrosis is associated with high leptin levels in chronic hepatitis C.", J. Viral Hepatitis, 2004, vol. 11, pp. 91-96. (Year: 2004).
Eun-Jeon Park et al, "Skullcapflavone I from Scutellaria baicalensis induces apoptosis in activated rat hepatic stellate cells", Planta Medica, Jan. 1, 2005 (Jan. 1, 2005), pp. 885-887.
Han-Soo Kim et al., "Chromone scaffold—mediated reprogramming of the epithelial—mesenchymal transition prevents fibrosis", bioRxiv, Feb. 17, 2017, preprint doi: https://doi.org/10.1101/106591.

* cited by examiner

USE OF EUPATILIN AS PHARMACEUTICAL COMPOSITION FOR PREVENTION AND TREATMENT OF FIBROSIS USING EMT INHIBITORY ACTIVITY

CROSS REFERENCE TO PRIOR APPLICATIONS

This application is a continuation Application of U.S. patent application Ser. No. 15/347,795 filed on Nov. 10, 2016 under 35 U.S.C. § 120, which claims priority to Korean Patent Application Nos. 10-2016-0020673 filed on Feb. 22, 2016, 10-2016-0032719 filed on Mar. 18, 2016, 10-2016-0062556 filed on Mar. 23, 2016, and 10-2016-0118158 filed on Sep. 13, 2016, which are all hereby incorporated by reference in their entirety.

BACKGROUND

1. Field of the Invention

The present invention relates to a new use of a chromone derivative as a pharmaceutical composition for the prevention and treatment of fibrosis using epithelial mesenchymal transition (EMT) inhibitory activity and, more particularly, to the novel use of a chromone derivative as an agent for the prevention and treatment of fibrosis, using the activity of the chromone derivative, which has been newly found to inhibit EMT.

2. Description of the Related Art

Fibrosis is a disease in which excess fibrous connective tissue is formed in an organ or tissue in a reparative or developmental process, such fibrous connective tissue being distinguished from normally formed fibrous tissue. When excess fibrous connective tissue is formed in an organ or tissue, the tissue becomes hard and the inflow of body fluids may decrease, making it impossible to sufficiently perform inherent living functions. It is known to be caused by injuries, inflammation, burns, radiation, chemotherapy, lymphedema, etc. Problems related to fibrosis may vary depending on the location at which fibrous connective tissue is formed, and the liver, glands, and lungs are mainly damaged. Typical examples of fibrosis include idiopathic pulmonary fibrosis (IPF), myelofibrosis, liver fibrosis, and kidney fibrosis.

Idiopathic pulmonary fibrosis is an interstitial lung disease, which chronically progresses and has a bad prognosis and for which therapeutic methods have not yet been proven. It is diagnosed when a honeycomb shape or an irregular shape is observed in a lung biopsy. Dyspnea gradually occurs, and hypoxia or myocardial infarction is caused, undesirably leading to death. The causes thereof have not been determined to date, but are considered to be due to various factors, such as the environment, viruses, heredity, toxic compounds, etc., to thus incur inflammation in the lungs, and fibrous cells are excessively manipulated during the recovery of such inflammation, whereby fibrosis progresses in the lungs.

Myelofibrosis is a bone marrow disorder in which excessive fibrous tissue formation occurs, thus disrupting the production of blood cells and changing the numbers of erythrocytes and leukocytes and the action thereof. It includes idiopathic myelofibrosis and secondary myelofibrosis. Specifically, idiopathic myelofibrosis exhibits severe fibroplasias of the systemic bone marrow, hypertrophy symptoms, and immature granulocytes or nucleated erythrocytes in the peripheral blood. The cause thereof is not obvious, but is deemed to be due to poisoning of the bone marrow, inflammation, etc. Secondary myelofibrosis is caused during the progression of leukemia, malignant lymphoma, bone marrow metastasis of cancer, poisoning by chemicals, etc. Effective therapeutic agents therefor have not yet been developed.

Liver fibrosis is also referred to as "liver cirrhosis", and is a disease in which the function of the liver is deteriorated due to the conversion of normal liver tissue into fibrotic tissue, such as regenerative nodules, because of chronic inflammation. It mainly occurs when the inflammatory state of the liver continues due to chronic hepatitis B or C, excessive alcohol consumption, or hepatotoxic substances. The treatment thereof aims to slow the progression of symptoms as much as possible. Although antiviral drugs may be used depending on the causes thereof, the effects thereof are unknown for different cases.

Kidney fibrosis is a progressive disease in which extracellular matrix accumulates, thus causing fibrosis in the kidneys, and includes glomerular sclerosis and tubular interstitial fibrosis. Side effects occur in the kidneys due to the fibrosis of the kidneys. It is caused by trauma, infection, surgery, environmental factors, chemicals, radiation exposure, etc., and may give rise to symptoms such as pain, urinary issues, nausea, vomiting, etc. Although such symptoms are controlled using drugs or via kidney transplantation, there is a need to develop an effective therapeutic agent therefor.

Meanwhile, Grande et al. recently reported research results in which Twist and Snail, main regulators of epithelial mesenchymal transition (hereinafter, referred to as "EMT"), play an important role in fibrosis of the kidneys, and Lovisa et al. also reported that EMT has a strong effect on kidney fibrosis. EMT refers to the phenomenon by which normal cells undergo genetic reprogramming in the form of mesenchymal cells, which are easily transportable due to changes in the cytoskeleton in intermediate stages during transformation into tumor cells. Hence, metastasis and the proliferation of tumors are considered to be suppressed when the expression of EMT-associated proteins is inhibited, and thus thorough research into EMT is being carried out in order to develop tumor therapeutic agents. Hundreds of EMT regulators, including Twist, Snail, Slug, E-Cadherin, Vimentin, Collagen1 $\alpha$1, etc., are known.

Suzuki et al. reported that DEC2 (BHLHE41) is a transcriptional repressor of Twist, which is an EMT regulator, and when the expression of DEC2 is suppressed, EMT is activated, thus resulting in malignant tumors. Also, Sato et al. reported that DEC2 functions to inhibit the expression of Slug, which is an EMT regulator, to thus suppress the formation of malignant tumors induced by TGF-$\beta$. In addition thereto, many researchers have reported the association of an EMT regulator with cancer metastasis using DEC2.

Research into EMT and EMT regulators has been mainly carried out for cancers or tumors. However, the present inventors have paid attention to the correlation between EMT and fibrosis based on some conventional research results and thus have conceived the notion that if EMT can be regulated, fibrosis can be prevented and treated.

Meanwhile, natural compounds having a chromone (chromen-4-one, 4H-chromen-4-one) structure are typically exemplified by eupatilin, wogonin, myricetin and the like, among which eupatilin is known to be contained in *Artemisia asiatica*, and has been mainly studied for its anticancer effects.

The present inventors have paid attention to the correlation between EMT and fibrosis and the correlation between DEC2 and EMT and have researched the possibility of using a chromone derivative, including eupatilin, as a therapeutic agent for fibrosis, based on the observation that eupatilin is able to upregulate DEC2 mRNA of macrophages differentiated from bone marrow cells. The inhibitory effect of the chromone derivative on EMT has been newly proven based on cell models and animal models, and fibrosis of the organs or tissues due to the activation of EMT may be effectively inhibited by such compounds, thus culminating in the present invention.

CITATION LIST

Non-Patent Literature

Grande M T, Sanchez-Laorden B, Lopez-Blau C, De Frutos C A, Boutet A, Arevalo M, Rowe R G, Weiss S J, Lopez-Novoa J M, Nieto M A. Snail1-induced partial epithelial-to-mesenchymal transition drives renal fibrosis in mice and can be targeted to reverse established disease. Nat Med. 2015 September; 21(9): 989-97.

Lovisa S, LeBleu V S, Tampe B, Sugimoto H, Vadnagara K, Carstens J L, Wu C C, Hagos Y, Burckhardt B C, Pentcheva-Hoang T, Nischal H, Allison J P, Zeisberg M, Kalluri R. Epithelial-to-mesenchymal transition induces cell cycle arrest and parenchymal damage in renal fibrosis. Nat Med. 2015 September; 21 (9):998-1009.

Suzuki M, Sato F, Bhawal U K. The basic helix-loop-helix (bHLH) transcription factor DEC2 negatively regulates Twist1 through an E-box element. Biochem Biophys Res Commun. 2014 Dec. 12; 455(3-4):390-5.

Sato F, Kawamura H, Wu Y, Sato H, Jin D, Bhawal U K, Kawamoto T, Fujimoto K, Noshiro M, Seino H, Morohashi S, Kato Y, Kijima H. The basic helix-loop-helix transcription factor DEC2 inhibits TGF-β-induced tumor progression in human pancreatic cancer BxPC-3 cells. Int J Mol Med. 2012 September; 30(3):495-501.

Dong Y, Geng Y, Li L, Li X, Yan X, Fang Y, Li X, Dong S, Liu X, Li X, Yang X, Zheng X, Xie T, Liang J, Dai H, Liu X, Yin Z, Noble P W, Jiang D, Ning W. Blocking follistatin-like 1 attenuates bleomycin-induced pulmonary fibrosis in mice. J Exp Med. 2015 Feb. 9; 212 (2):235-52.

SUMMARY

Accordingly, the present invention has been made keeping in mind the above problems encountered in the related art, and the present invention is intended to provide the novel use of a chromone derivative as an agent for the prevention and treatment of fibrosis.

In addition, the present invention is intended to provide a novel pharmaceutical composition for the prevention and treatment of fibrosis.

In addition, the present invention is intended to provide a method of effectively preventing and treating fibrosis.

An aspect of the present invention provides a pharmaceutical composition for the prevention and treatment of a disease caused by fibrosis of an organ or tissue in vivo, containing, as an active ingredient, a compound selected from among a chromone derivative represented by Chemical Formula 1 below and a pharmaceutically acceptable salt thereof.

[Chemical Formula 1]

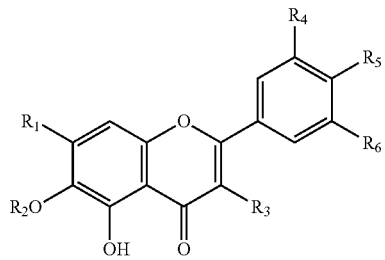

In Chemical Formula 1, $R_1$ is hydrogen, a hydroxyl group, a methoxy group, a trifluoromethyl group or an acetoxy group, $R_2$ is a methyl group, an ethyl group, a cyclopentyl group, a cyclohexyl group, a phenyl group or a benzyl group, $R_3$ is hydrogen, an ethyl group, an acetyl group, an acetoxy group, a carboxyl group, a benzoyloxy group or a 3,4,5-trihydroxybenzoyloxy group, and $R_4$ to $R_6$ are each independently hydrogen, a hydroxyl group, a methyl group, a methoxy group, an acetoxy group, a carboxyl group or a benzoyloxy group.

The pharmaceutical composition of the present invention is particularly effective for the prevention and treatment of a disease caused by the fibrosis of an organ or tissue in vivo, especially a disease selected from the group consisting of idiopathic pulmonary fibrosis, myelofibrosis, liver fibrosis, and kidney fibrosis.

Preferably, in the pharmaceutical composition of the present invention, $R_1$ is a hydroxyl group or a methoxy group, $R_2$ is a methyl group, $R_3$ is hydrogen, $R_5$ is a hydroxyl group or a methoxy group, and $R_4$ and $R_6$ are each independently hydrogen, a hydroxyl group, or a methoxy group.

In the pharmaceutical composition of the present invention, the chromone derivative may be any one selected from among 2-(3,4-dimethoxyphenyl)-5,7-dihydroxy-6-methoxy-chromone (eupatilin, Chemical Formula 2), 2-(3,4-dihydroxyphenyl)-5,7-dihydroxy-6-methoxy-chromone (Chemical Formula 3), 5,7-dihydroxy-2-(4-hydroxy-3-methoxyphenyl)-6-methoxy-chromone (Chemical Formula 4), 5,7-dihydroxy-2-(4-hydroxyphenyl)-6-methoxy-chromone (Chemical Formula 5), 5-hydroxy-2-(4-hydroxyphenyl)-6,7-dimethoxy-chromone (Chemical Formula 6), and 2-(3,4-dihydroxyphenyl)-5-hydroxy-6,7-dimethoxy-chromone (Chemical Formula 7).

[Chemical Formula 2]

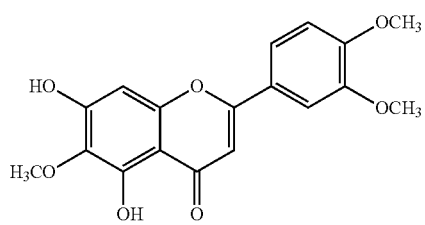

-continued

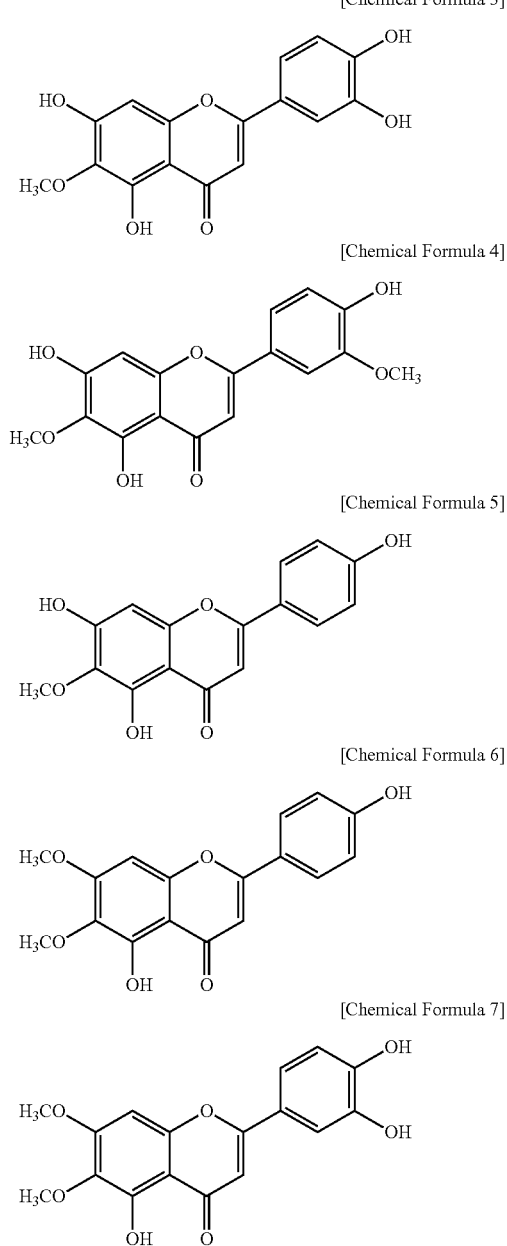

According to the present invention, a pharmaceutical composition contains a chromone derivative of Chemical Formula 1 as an active ingredient, thus effectively inhibiting the activation of EMT to thereby enable the effective suppression of fibrosis of an organ or tissue due to the activation of EMT. In particular, cells that have already undergone fibrosis can be restored to their original normal condition, whereby the middle or late stage of fibrosis can be treated, in addition to the prevention of fibrosis or initial response thereto.

BRIEF DESCRIPTION OF THE DRAWINGS

The above and other features and advantages of the present invention will be more clearly understood from the following detailed description taken in conjunction with the accompanying drawings, in which.

DETAILED DESCRIPTION

According to conventional research results in which EMT plays an important role in kidney fibrosis (Grande et al., 2015 and Lovisa et al., 2015) and EMT may be regulated by DEC2 (Suzuki et al., 2014 and Sato et al., 2012), correlations between EMT and fibrosis and between DEC2 and EMT have been receiving attention. If DEC2 may be adjusted, it is possible to regulate EMT, and consequently fibrosis is deemed to be prevented and treated.

DEC2 is known to be a transcriptional repressor of Twist and Slug, which are EMT regulators. If the expression of DEC2 may be increased, the expression of the EMT regulator is inhibited, whereby EMT is suppressed, ultimately inhibiting fibrosis.

Figure 2:
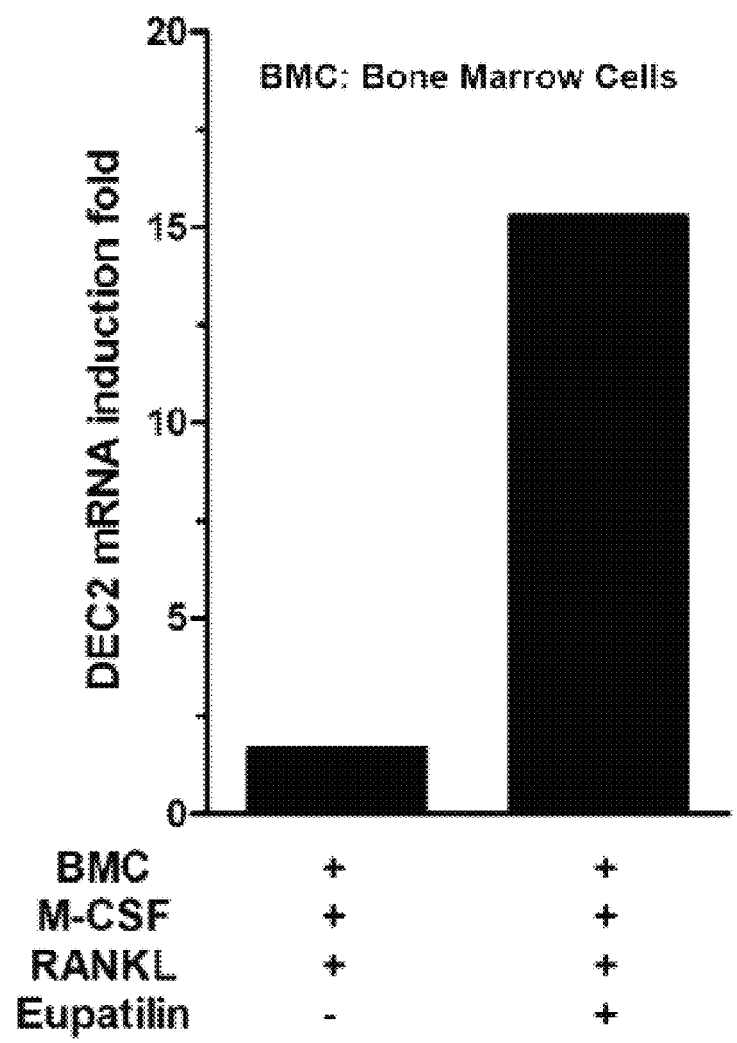
FIG. 2 is a graph showing the effect of increasing DEC2 mRNA expression of eupatilin in macrophages differentiated from bone marrow cells.

Therefore, based on the results of measurement of the DEC2 expression control potential of eupatilin among chromone derivatives according to the present invention, eupatilin can be found to significantly increase the mRNA expression of DEC2 to thus enable the treatment of fibrosis (FIG. 2).

Figure 3:
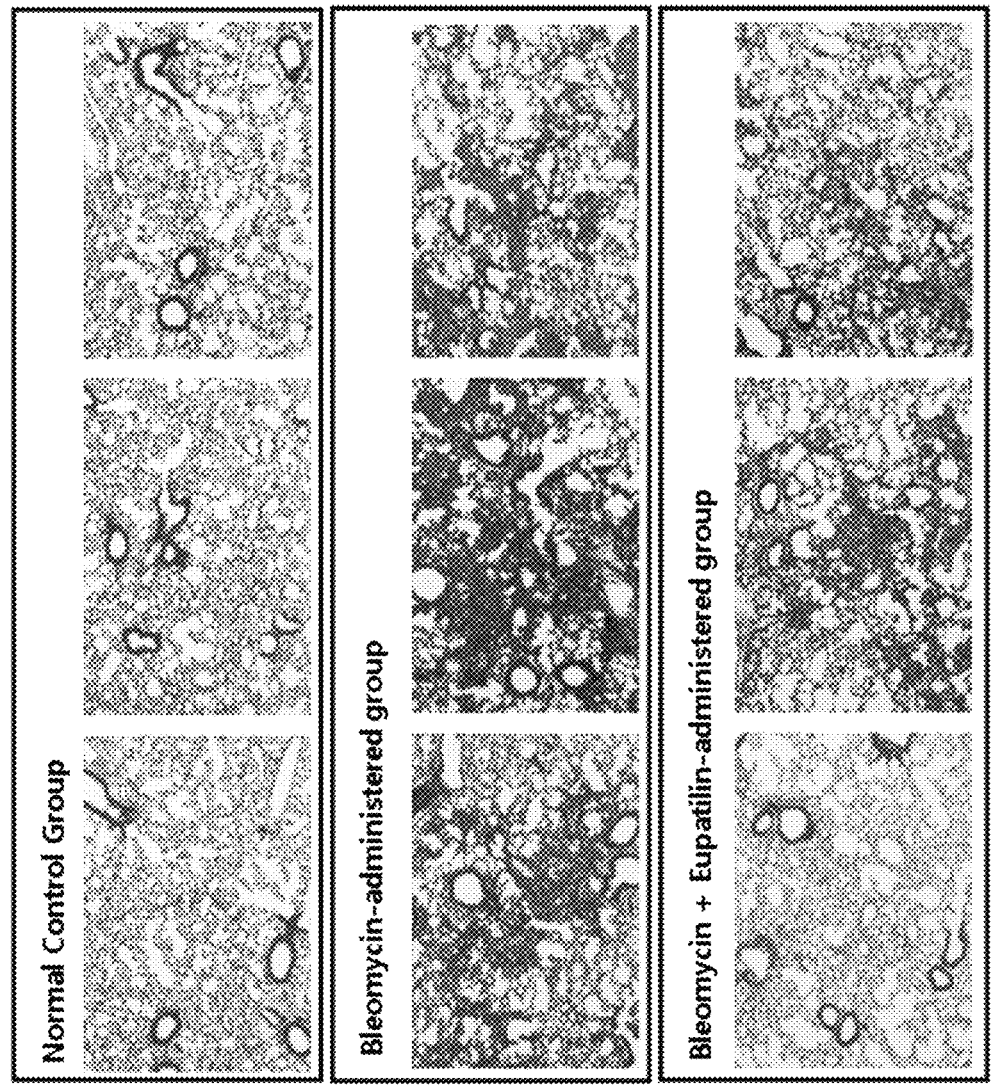
FIG. 3 is of images showing the effect of eupatilin on the inhibition of fibrosis, in which three pieces of lung tissue from a single mouse in each test group were recovered, subjected to Masson's trichrome staining and then observed with a microscope, a normal control group is a normal mouse group to which bleomycin and eupatilin were not administered but only a vehicle was administered, a bleomycin-administered group is a mouse group to which bleomycin was administered to thus induce pulmonary fibrosis, and a bleomycin+eupatilin-administered group is a mouse group to which bleomycin was administered to thus induce pulmonary fibrosis and to which eupatilin (40 μg) was also administered.

In order to more clearly evaluate the fibrosis treatment potential of eupatilin, bleomycin was administered to the lungs of a mouse to induce pulmonary fibrosis, and the effect of eupatilin was measured. As the result thereof, eupatilin can be found to effectively inhibit fibrosis of lung tissue induced by bleomycin to thus enable the practical inhibition of fibrosis of lung tissue, such as idiopathic pulmonary fibrosis (FIG. 3).

Figure 4:
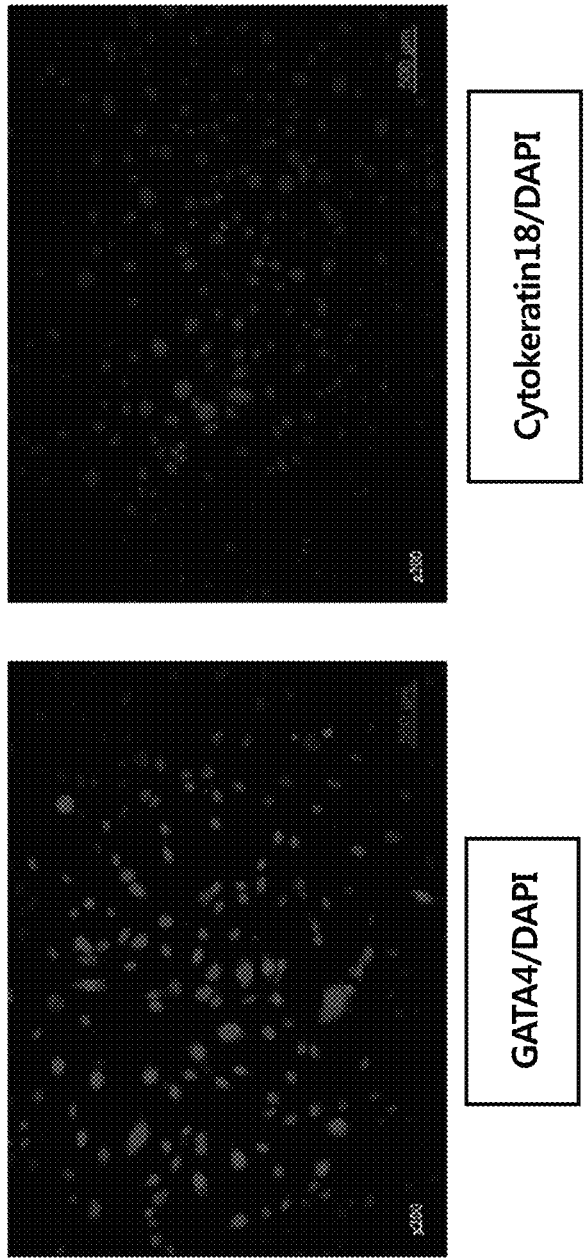
FIG. 4 shows the results of IHC (Immunohistochemistry) of an ONGHEPA1 cell line manufactured from a fibrosis cell model, in which the cell line is cells derived from mesoderm and is not hepatocytes but hepatic stellate cells (HSC), the left illustrating IHC results using a positive anti-GATA4 antibody response and the right illustrating MC results using a negative anti-CK-18 antibody response.
Figure 5:
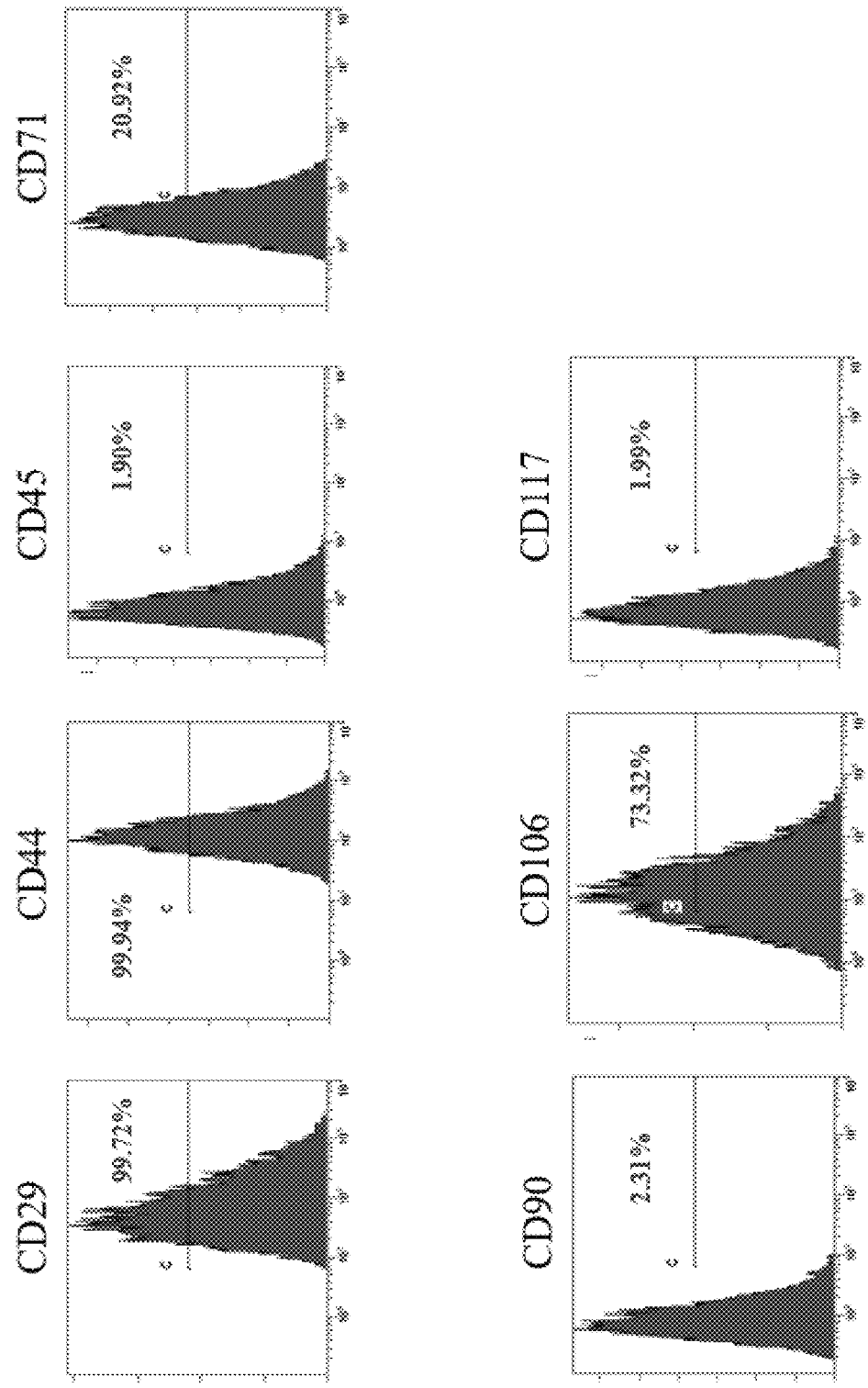
FIG. 5 shows the results of FACS (Fluorescence-Activated Cell Sorting) of an ONGHEPA1 cell line, in which ONGHEPA1 expresses CD29, CD44, CD71 and CD106, which are membrane proteins, as mesenchymal stem cells of the liver.

Furthermore, in order to determine whether eupatilin is able to inhibit fibrosis of tissues other than pulmonary fibrosis, attention was paid to HSC, which is known to be closely associated with liver fibrosis, as a model therefor. HSC ceases to work under normal conditions and is then activated by a cell growth factor such as TGF-β or PDGF when hepatic cells are damaged due to stress such as inflammation, thus producing a large amount of extracellular matrix (ECM) to thereby harden tissue and differentiate HSC itself into myofibroblasts (MFB), undesirably casing tissue fibrosis. Thus, when immortalized cells of HSC are obtained and treated with TGF-β, fibrosis may be induced, and thus HSC is considered to be a useful model for fibrosis. Consequently, immortalized HSC was obtained, and the cell line, which is practically differentiated 100% into MFB by the addition of TGF-β, was established (FIGS. 4 and 5). This cell line is called ONGHEPA1 (KCTC13086BP).

Figure 6:
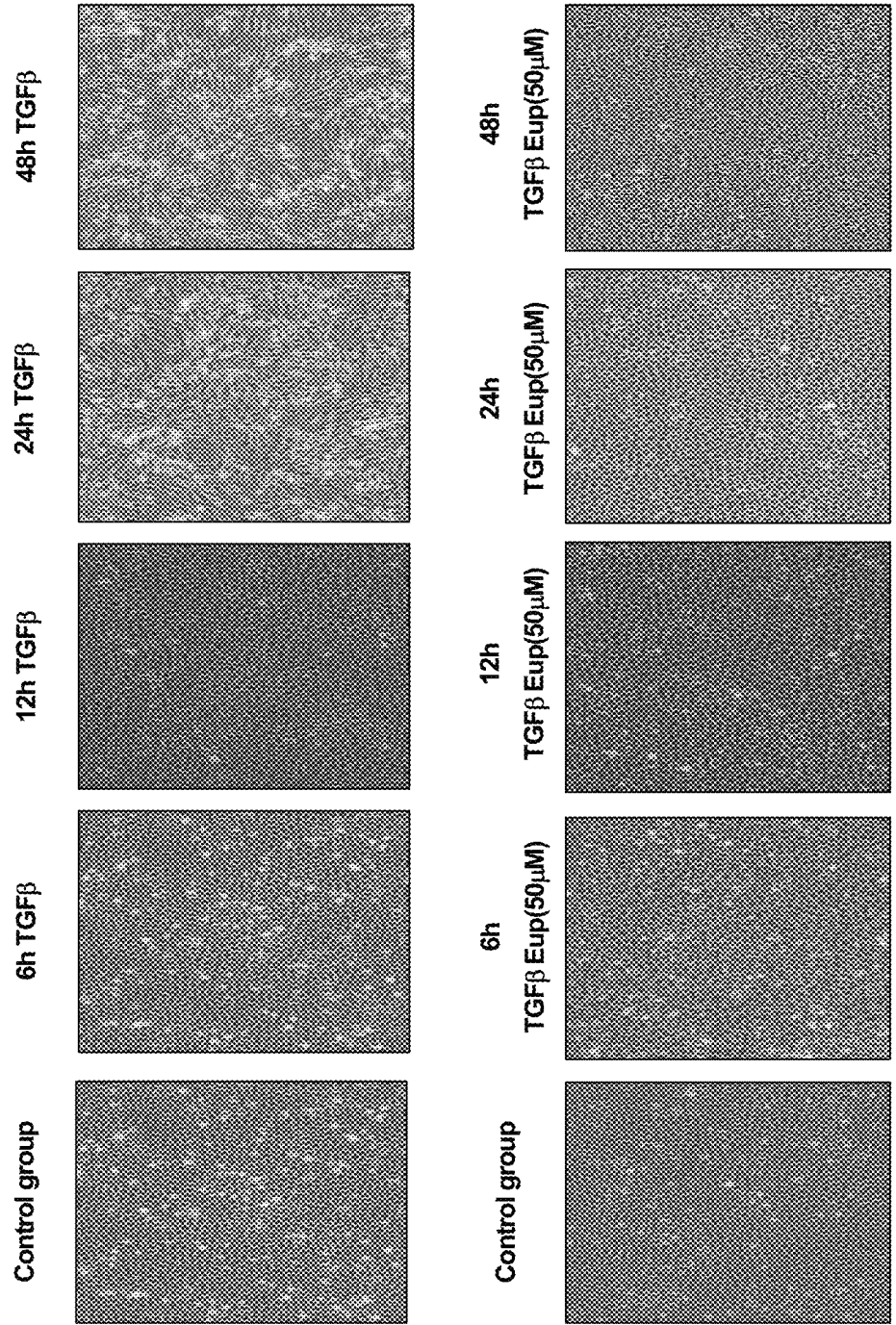
FIG. 6 is of microscope images showing the test results of the fibrosis-inhibiting effect upon treatment with eupatilin (which is abbreviated to "Eup" in the drawings) depending on the incubation time of ONGHEPA1 cells (6 hr, 12 hr, 24 hr, and 48 hr) and treatment with a drug, in which a control group is a group in which ONGHEPA1 cells were incubated without additional treatment, 6 h TGFβ to 48 h TGFβ are test groups to which a culture medium was added with TGF-β (5 ng/mL, TGF-β is used at a concentration of 5 ng/mL in the other drawings) and in which ONGHEPA1 cells were incubated for 6 to 48 hr, and 6 h TGFβ Eup (50 μM) to 48 h TGFβ Eup (50 μM) are test groups to which a culture medium was added with TGF-β and eupatilin (50 μM, eupatilin and a chromone derivative are used at a concentration of 50 μM in the other drawings) and in which ONGHEPA1 cells were incubated for 6 to 48 hr.
Figure 7:
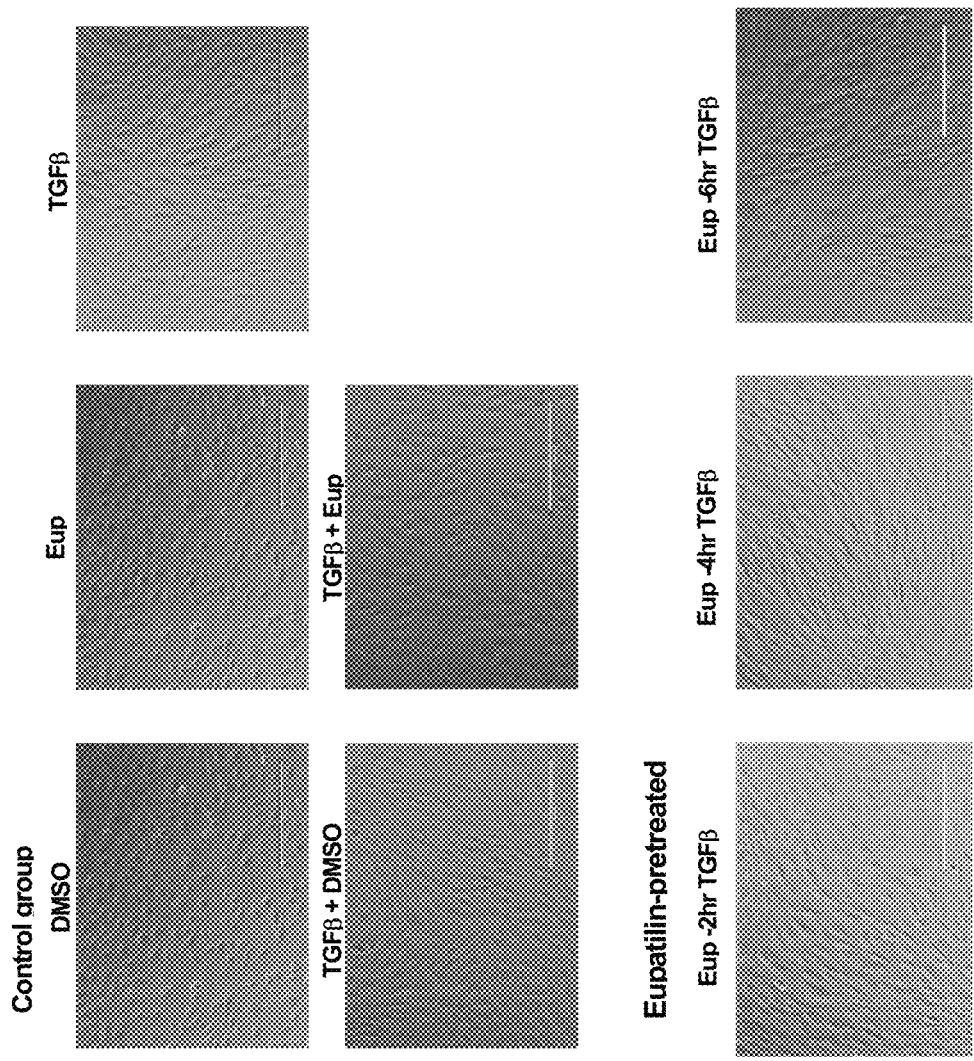
FIG. 7 is of microscope images showing the test results of the effect of eupatilin on the inhibition of fibrosis when ONGHEPA1 cells were first treated with eupatilin, washed to remove eupatilin and then treated with TGF-β to induce fibrosis, in which DMSO is a control group in which a culture medium was added with DMSO (a solvent for eupatilin) and ONGHEPA1 cells were incubated for 24 hr, Eup is a control group in which a culture medium was added with eupatilin and ONGHEPA1 cells were incubated for 24 hr, TGFβ is a control group in which a culture medium was added with TGF-β and ONGHEPA1 cells were incubated for 24 hr, TGFβ+DMSO is a control group in which a culture medium was added with TGF-β and DMSO and ONGHEPA1 cells were incubated for 24 hr, TGFβ+Eup is a control group in which a culture medium was added with TGF-β and eupatilin and ONGHEPA1 cells were incubated for 24 hr, and Eup-2 hr TGFβ to Eup-6 hr TGFβ are test groups in which a culture medium was added with eupatilin and ONGHEPA1 cells were incubated for 2 to 6 hr, washed to remove eupatilin, added with TGF-β, and incubated for 24 hr.

Based on the results of measurement of the fibrosis-inhibiting effect of eupatilin using such ONGHEPA1 cells, eupatilin can be found to effectively inhibit fibrosis induced by the addition of TGF-β to thus enable the practical inhibition of fibrosis of liver tissue, such as liver fibrosis (FIG. 6). Also, when ONGHEPA1 cells were pretreated with eupatilin, washed to remove eupatilin, and treated with TGF-β to induce fibrosis, no changes were observed. Therefore, eupatilin can also be found to have no influence on normal HSC (FIG. 7).

Figure 8:
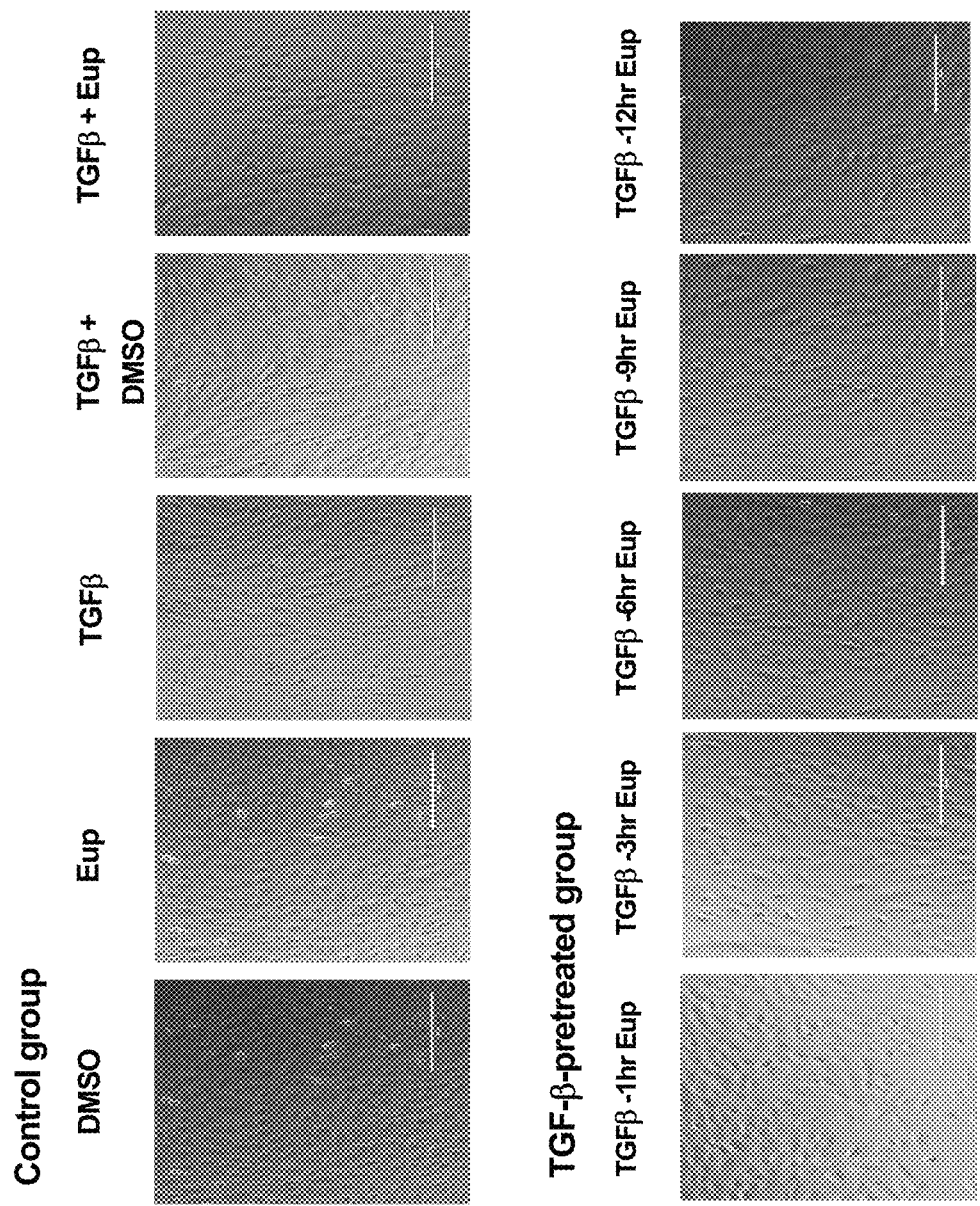
FIG. 8 is of microscope images showing the test results of the effect of eupatilin on the inhibition of fibrosis when ONGHEPA1 cells were first treated with TGF-β to induce fibrosis, washed to remove TGF-β and then treated with eupatilin, in which DMSO is a control group in which a culture medium was added with DMSO (a solvent for eupatilin) and ONGHEPA1 cells were incubated for 24 hr, Eup is a control group in which a culture medium was added with eupatilin and ONGHEPA1 cells were incubated for 24 hr, TGFβ is a control group in which a culture medium was added with TGF-β and ONGHEPA1 cells were incubated for 24 hr, TGFβ+DMSO is a control group in which a culture medium was added with TGF-β and DMSO and ONGHEPA1 cells were incubated for 24 hr, TGFβ+Eup is a control group in which a culture medium was added with TGF-β and eupatilin and ONGHEPA1 cells were incubated for 24 hr, and TGFβ-1 hr Eup to TGFβ-12 hr Eup are test groups in which a culture medium was added with TGF-β and ONGHEPA1 cells were incubated for 1 to 12 hr, washed to remove TGF-β, added with eupatilin, and incubated for 24 hr.
Figure 9:
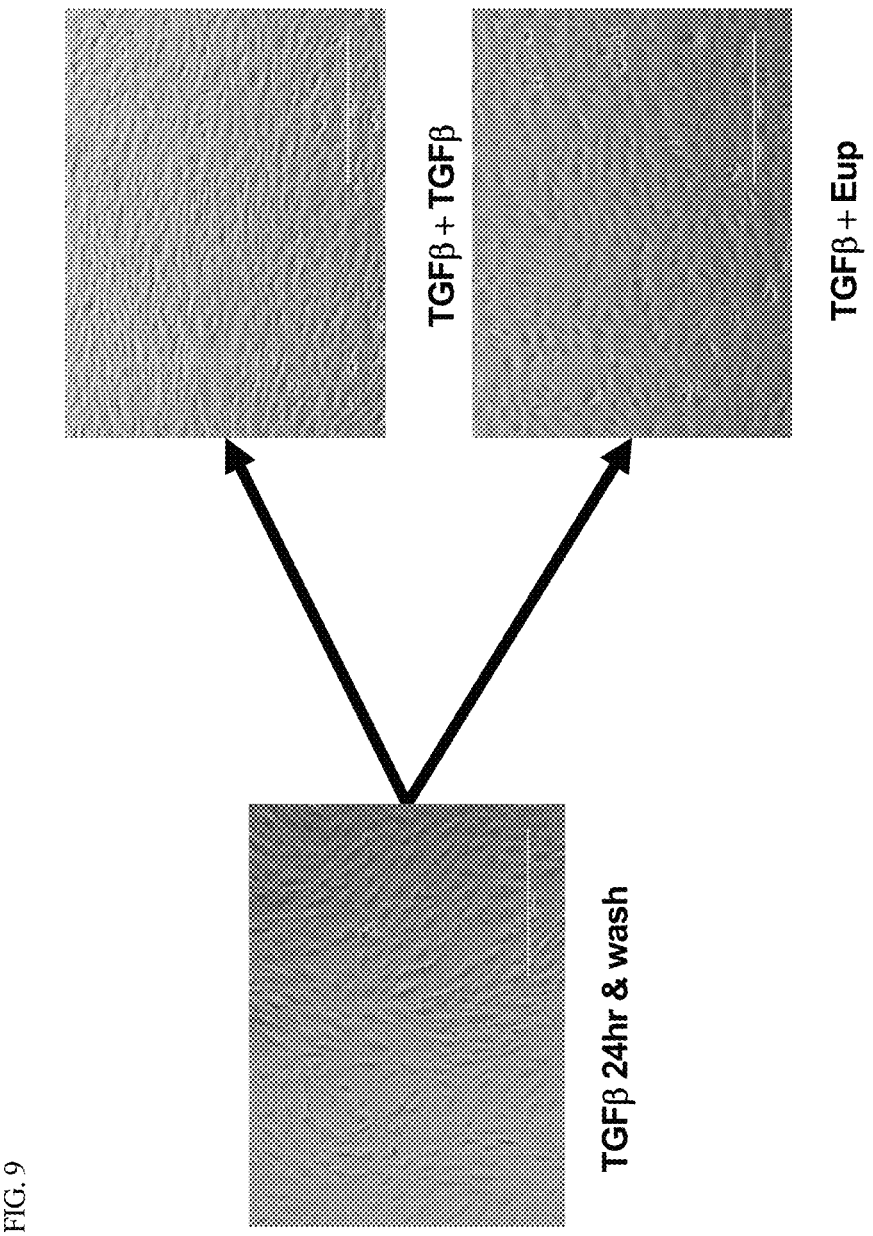
FIG. 9 is of microscope images showing the test results of the effect of eupatilin on reversing fibrosis when ONGHEPA1 cells were first treated with TGF-β to induce fibrosis, washed to remove TGF-β and then treated with eupatilin or TGF-β, in which TGFβ 24 hr & wash is a control group in which a culture medium was added with TGF-β and ONGHEPA1 cells were incubated for 24 hr, washed to remove TGF-β and incubated for 24 hr, TGFβ+TGFβ is a control group in which a culture medium was added with TGF-β and ONGHEPA1 cells were incubated for 24 hr, washed to remove TGF-β, further added with TGF-β, and incubated for 24 hr, and TGFβ+Eup is a test group in which a culture medium was added with TGF-β and ONGHEPA1 cells were incubated for 24 hr, washed to remove TGF-β, added with eupatilin (50 µM) and TGF-β and incubated for 24 hr.

Although eupatilin has been revealed to inhibit the progress of fibrosis through the measurement of the effect of eupatilin during the course of fibrosis of tissues or cells, there is a need to evaluate the effect of eupatilin on fibrosis that is already apparent. Thus, ONGHEPA1 cells were treated with TGF-β for a predetermined period of time to progress fibrosis, after which changes in the presence of eupatilin were measured, from which eupatilin can be found to restore ONGHEPA1 cells that have already undergone fibrosis to their original normal condition (FIGS. 8 and 9). This means that eupatilin is able to treat middle or late stages of fibrosis, as well as being useful in the prevention of fibrosis or initial response thereto.

Figure 10:
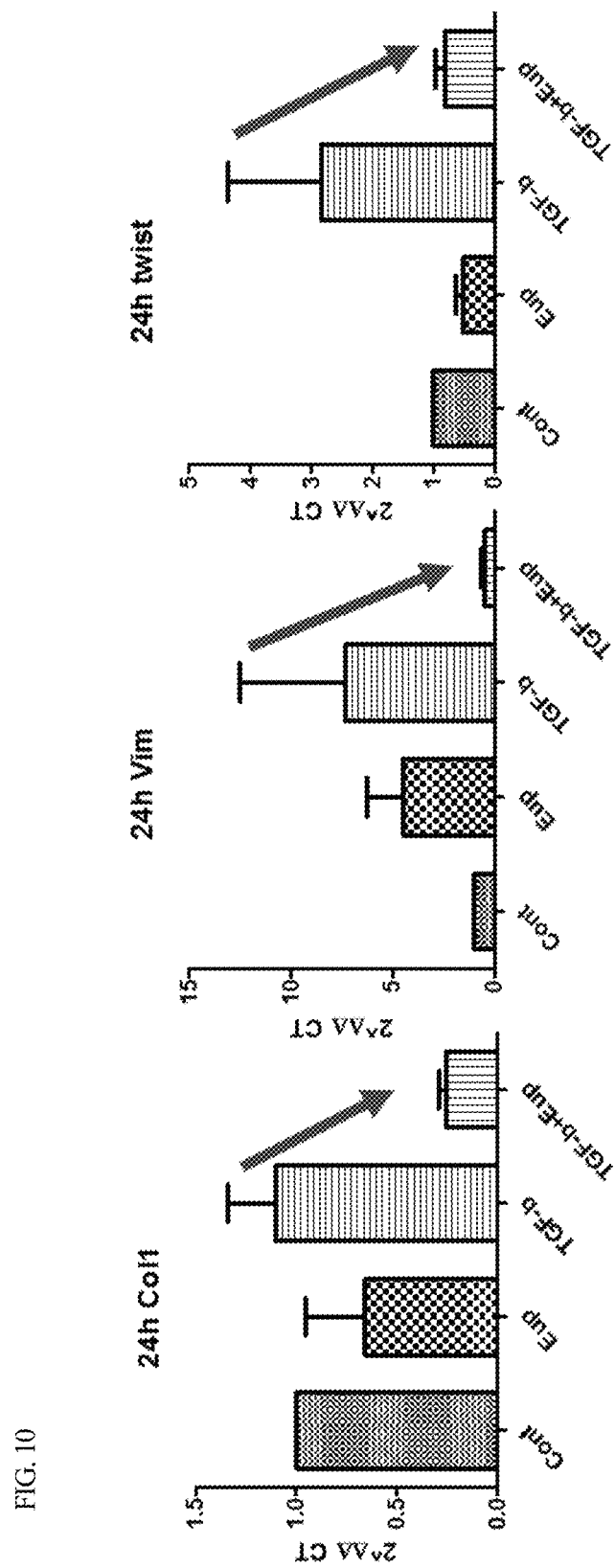
FIG. 10 is of graphs showing the test results of the effect of eupatilin on the inhibition of EMT, as real-time RT-PCR (Reverse Transcription Polymerase Chain Reaction) results obtained by analyzing the extent of expression of Col1, Vim and Twist depending on the treatment conditions of ONGHEPA1 cells, in which Cont is a control group in which ONGHEPA1 cells were incubated for 24 hr without additional treatment, Eup is a control group in which a culture medium was added with eupatilin and ONGHEPA1 cells were incubated for 24 hr, TGFβ is a control group in which a culture medium was added with TGF-β and ONGHEPA1 cells were incubated for 24 hr, and TGFβ+Eup is a test group in which a culture medium was added with TGF-β and eupatilin and ONGHEPA1 cells were incubated for 24 hr.

In order to evaluate whether fibrosis may be treated by inhibiting EMT as anticipated in the early research, the expression of EMT-associated factors, such as Col1 (type 1 Collagen), Vim (Vimentin) and Twist, was measured. As the result thereof, eupatilin can be found to inhibit the expression of these genes and thus to suppress EMT to thereby exhibit the fibrosis-inhibiting effect (FIG. 10).

Figure 13:
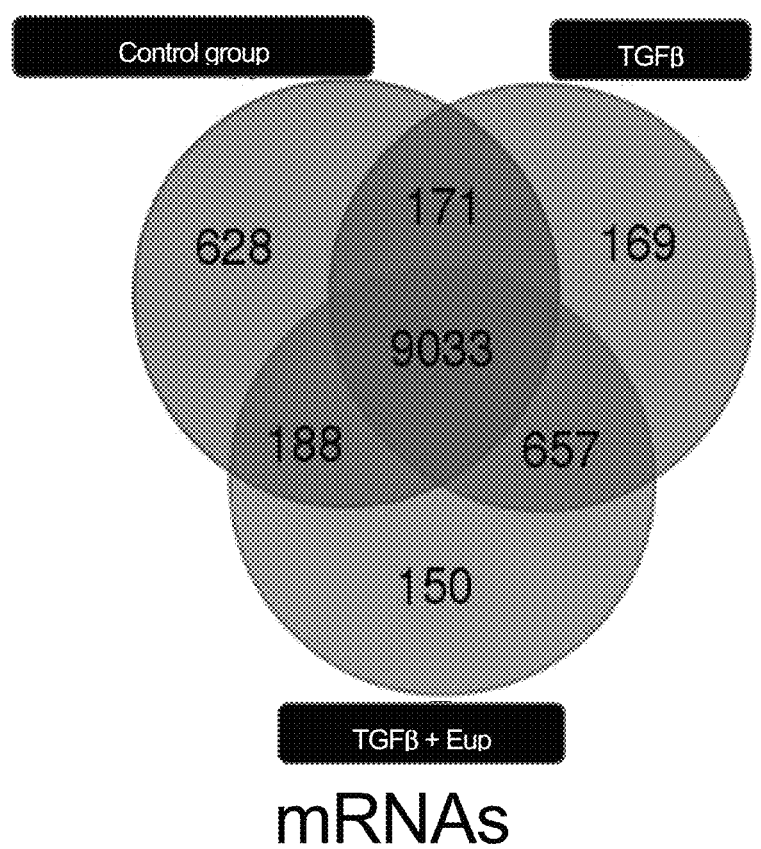
FIG. 13 shows the analysis results of transcriptome of ONGHEPA1 cells as a control group, fibrosis-induced ONGHEPA1 cells, and ONGHEPA1 cells in which fibrosis was induced and which were treated with eupatilin, a control group indicating ONGHEPA1 cells, TGFβ indicating a control group in which a culture medium was added with TGF-β and ONGHEPA1 cells were incubated for 24 hr, and TGFβ+Eup indicating a test group in which a culture medium was added with TGF-β and eupatilin and ONGHEPA1 cells were incubated for 24 hr.
Figure 14:
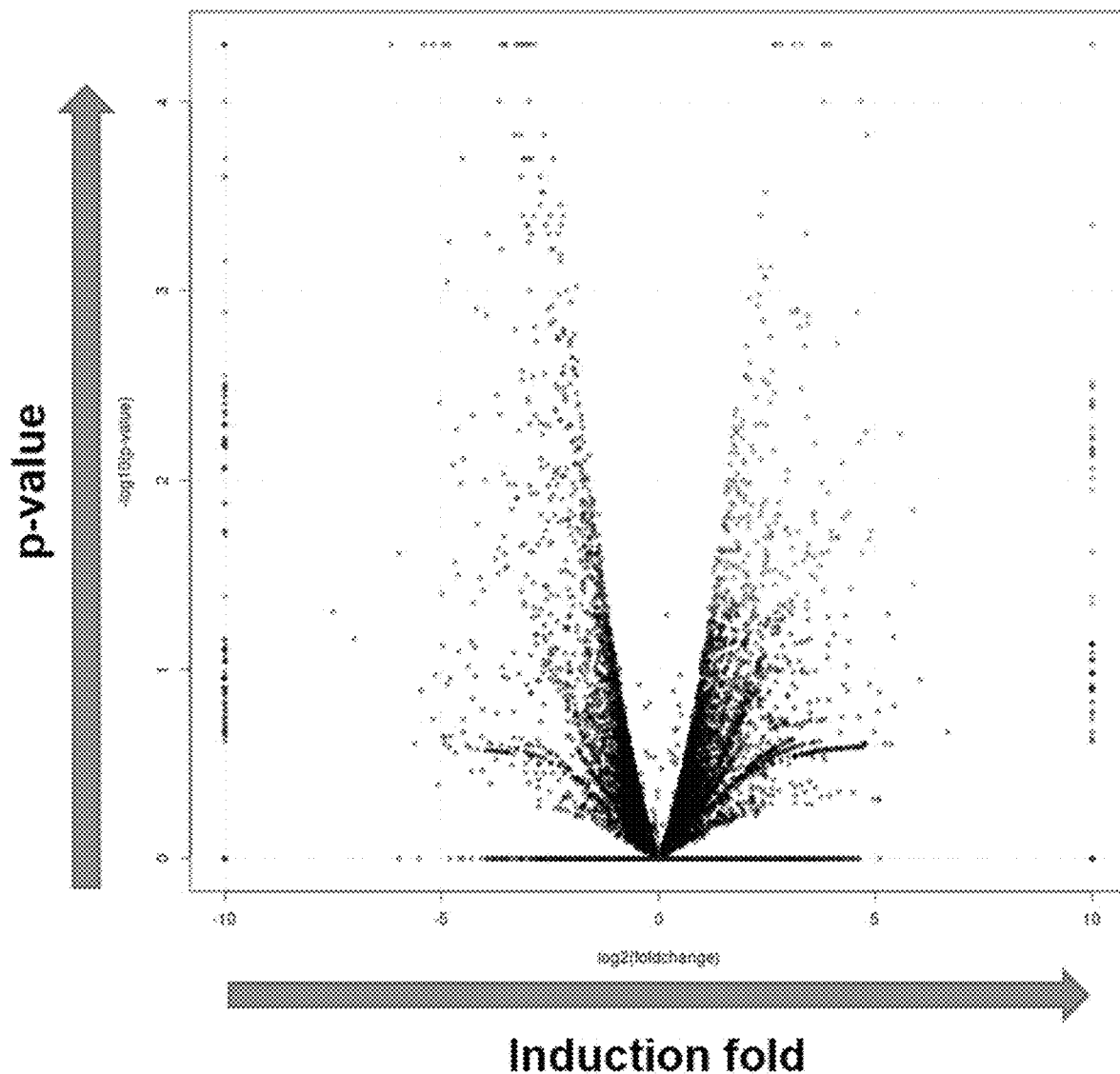
FIG. 14 shows a volcano plot depicting the p-value versus the induction fold of genes in which gene expression was changed in normal ONGHEPA1 cells, fibrosis-induced ONGHEPA1 cells, and ONGHEPA1 cells in which fibrosis was induced and which were treated with eupatilin.
Figure 15:
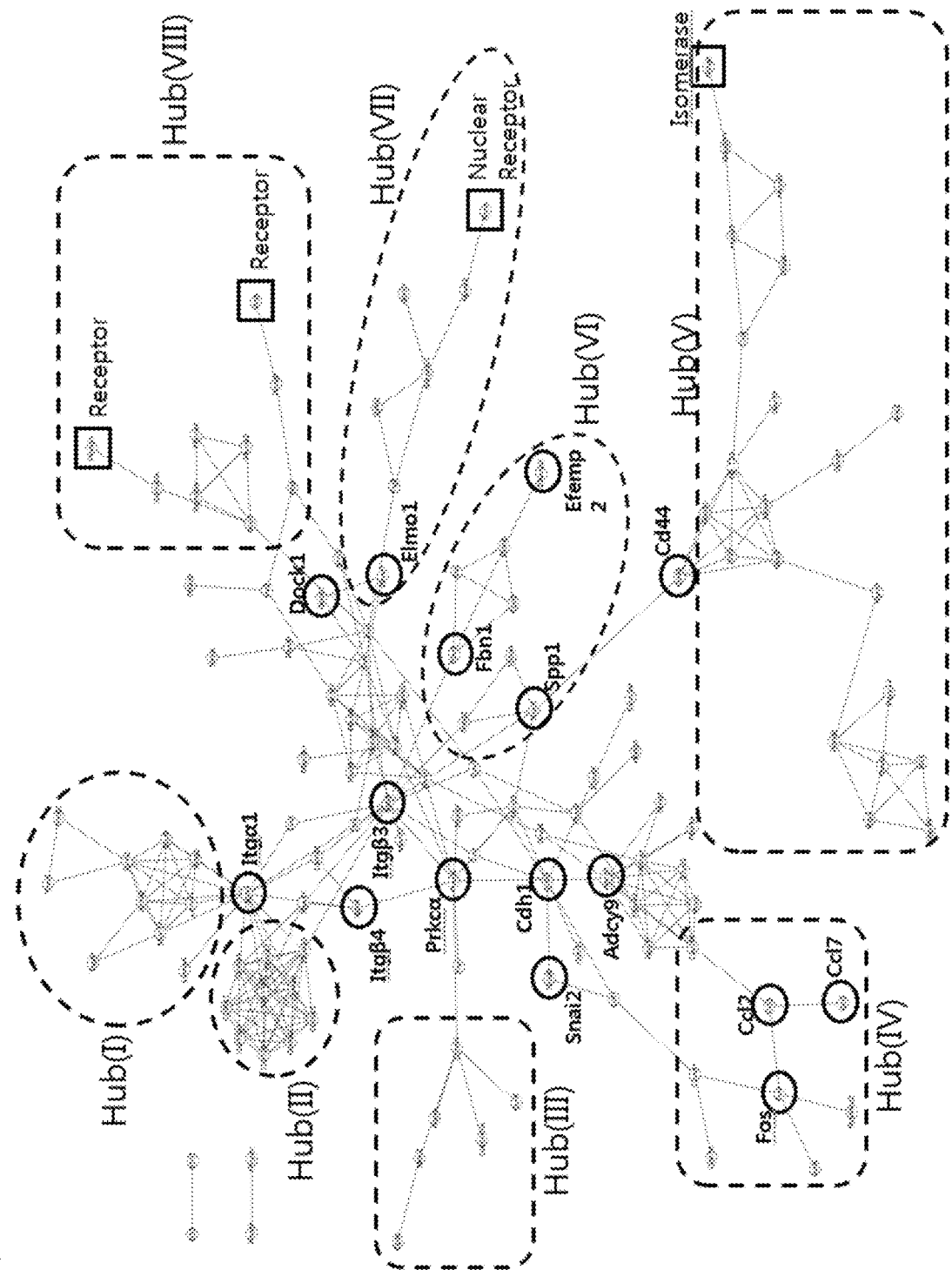
FIG. 15 shows the unbiased analysis results of the interactome of genes in which gene expression was significantly changed in normal ONGHEPA1 cells, fibrosis-induced ONGHEPA1 cells, and ONGHEPA1 cells in which fibrosis was induced and which were treated with eupatilin.

In order to more clearly evaluate whether the effect of eupatilin on the treatment of fibrosis is caused by the inhibition of EMT, total mRNA was analyzed when fibrosis was induced in normal cells and when fibrosis was inhibited by eupatilin, whereby genes that showed a significant difference in expression were investigated and the interactome between these genes was assayed. Therefore, eight gene network hubs were obtained, and these hubs were mostly composed of EMT-associated genes, and node genes for connecting these hubs are very important factors of EMT, from which the effect of eupatilin on the treatment of fibrosis can be concluded to result from the regulation of EMT (FIGS. 13 to 15).

Based on the results of analysis of genes having a large difference in expression among total mRNA assay results, the expression of 103 genes was greatly increased due to the induction of fibrosis by TGF-β, and fibrosis was inhibited by the addition of eupatilin, and thus gene expression was hardly observed. That is, these genes are regarded as target genes of eupatilin. Most of these genes are associated with EMT and are known to be important in terms of fibrosis based on conventional research results (Tables 2 to 5).

Particularly, there has been a research report on a Follistatin-like 1 (Fstl1) gene in which, when the expression of the gene was inhibited, even if pulmonary fibrosis was induced by bleomycin, pulmonary fibrosis was hardly observed (Dong et al., 2015). The results, in which the expression of Fstl1 is inhibited to a level of almost zero by eupatilin, more clearly show the effect of eupatilin on the treatment of pulmonary fibrosis and also support the use of eupatilin as a strong fibrosis therapeutic agent together with the aforementioned hypothesis.

Moreover, 103 such genes were expressed not only in HSC but also in other fibroblasts or cancer cells, from which eupatilin can be found to treat fibrosis of other tissues or cells, as well as liver fibrosis.

Figure 11:
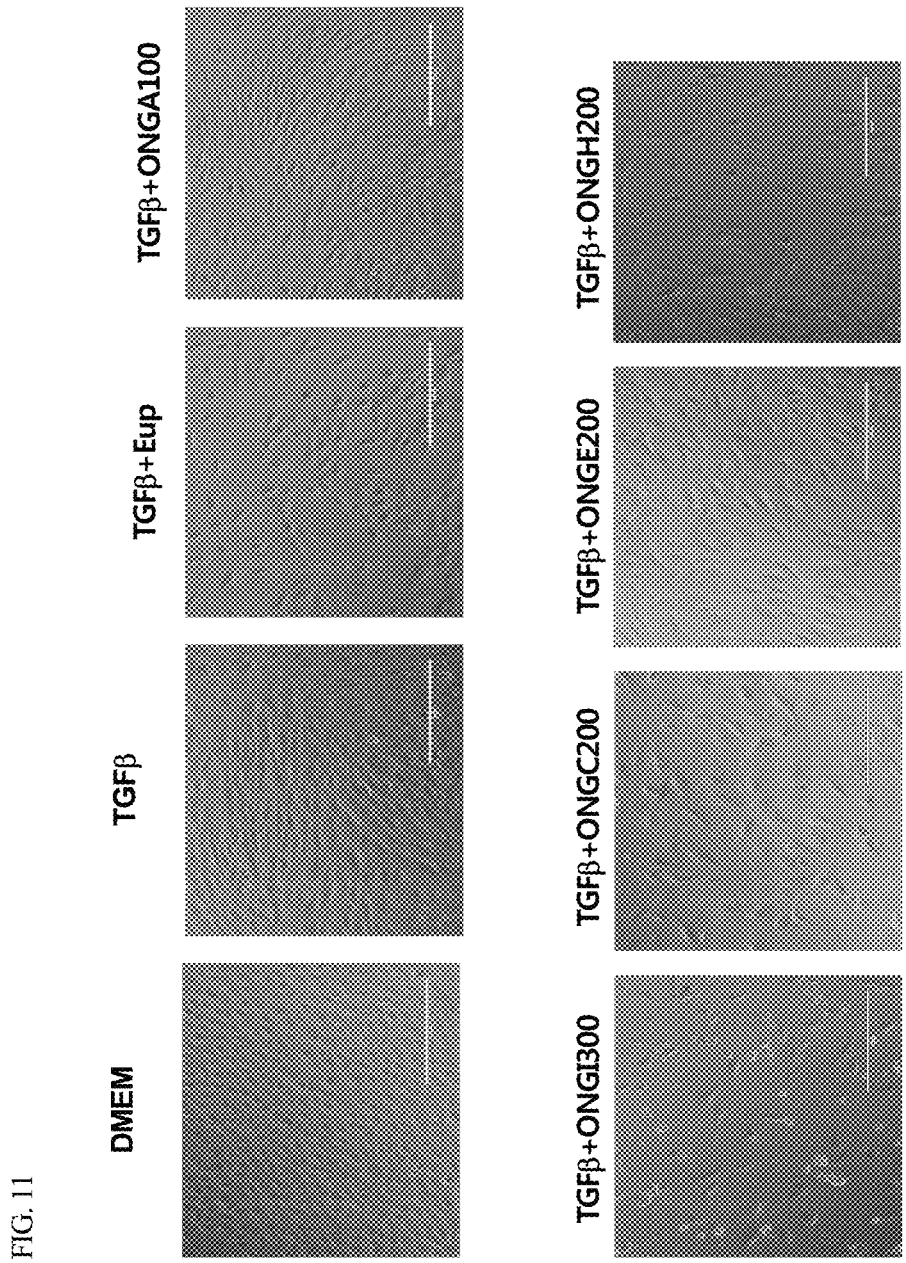
FIGS. 11 and 12 show microscope images of the test results of the effects of chromone derivatives on the inhibition of fibrosis when cells were treated with TGF-β to induce fibrosis and then treated with a 50 µM chromone derivative, in which DMEM is a control group in which ONGHEPA1 cells were incubated without additional treatment, TGFβ is a control group in which a culture medium was added with TGF-β and ONGHEPA1 cells were incubated for 24 hr, TGFβ+Eup is a control group in which a culture medium was added with TGF-β and eupatilin and ONGHEPA1 cells were incubated for 24 hr, TGFβ+ONGA100 is a test group in which a culture medium was added with TGF-β and ONGA100 (Chemical Formula 8) and ONGHEPA1 cells were incubated for 24 hr, TGFβ+ONGI300 is a test group in which a culture medium was added with TGF-β and ONGI300 (Chemical Formula 3) and ONGHEPA1 cells were incubated for 24 hr, TGFβ+ONGC200 is a test group in which a culture medium was added with TGF-β and ONGC200 (Chemical Formula 5) and ONGHEPA1 cells were incubated for 24 hr, TGFβ+ONGE200 is a test group in which a culture medium was added with TGF-β and ONGE200 (Chemical Formula 6) and ONGHEPA1 cells were incubated for 24 hr, TGFβ+ONGH200 is a test group in which a culture medium was added with TGF-β and ONGH200 (Chemical Formula 7) and ONGHEPA1 cells were incubated for 24 hr, TGFβ+wogonin is a test group in which a culture medium was added with TGF-β and wogonin (Chemical Formula 9) and ONGHEPA1 cells were incubated for 24 hr, TGFβ+ONGB200 is a test group in which a culture medium was added with TGF-β and ONGB200 (Chemical Formula 10) and ONGHEPA1 cells were incubated for 24 hr, TGFβ+ONGE300 is a test group in which a culture medium was added with TGF-β and ONGE300 (Chemical Formula 11) and ONGHEPA1 cells were incubated for 24 hr, TGFβ+ONGD200 is a test group in which a culture medium was added with TGF-β and ONGD200 (Chemical Formula 12) and ONGHEPA1 cells were incubated for 24 hr, TGFβ+ONGH300 is a test group in which a culture medium was added with TGF-β and ONGH300 (Chemical Formula 13) and ONGHEPA1 cells were incubated for 24 hr, and TGFβ+ONGD400 is a test group in which a culture medium was added with TGF-β and ONGD400 (Chemical Formula 14) and ONGHEPA1 cells were incubated for 24 hr.
Figure 12:
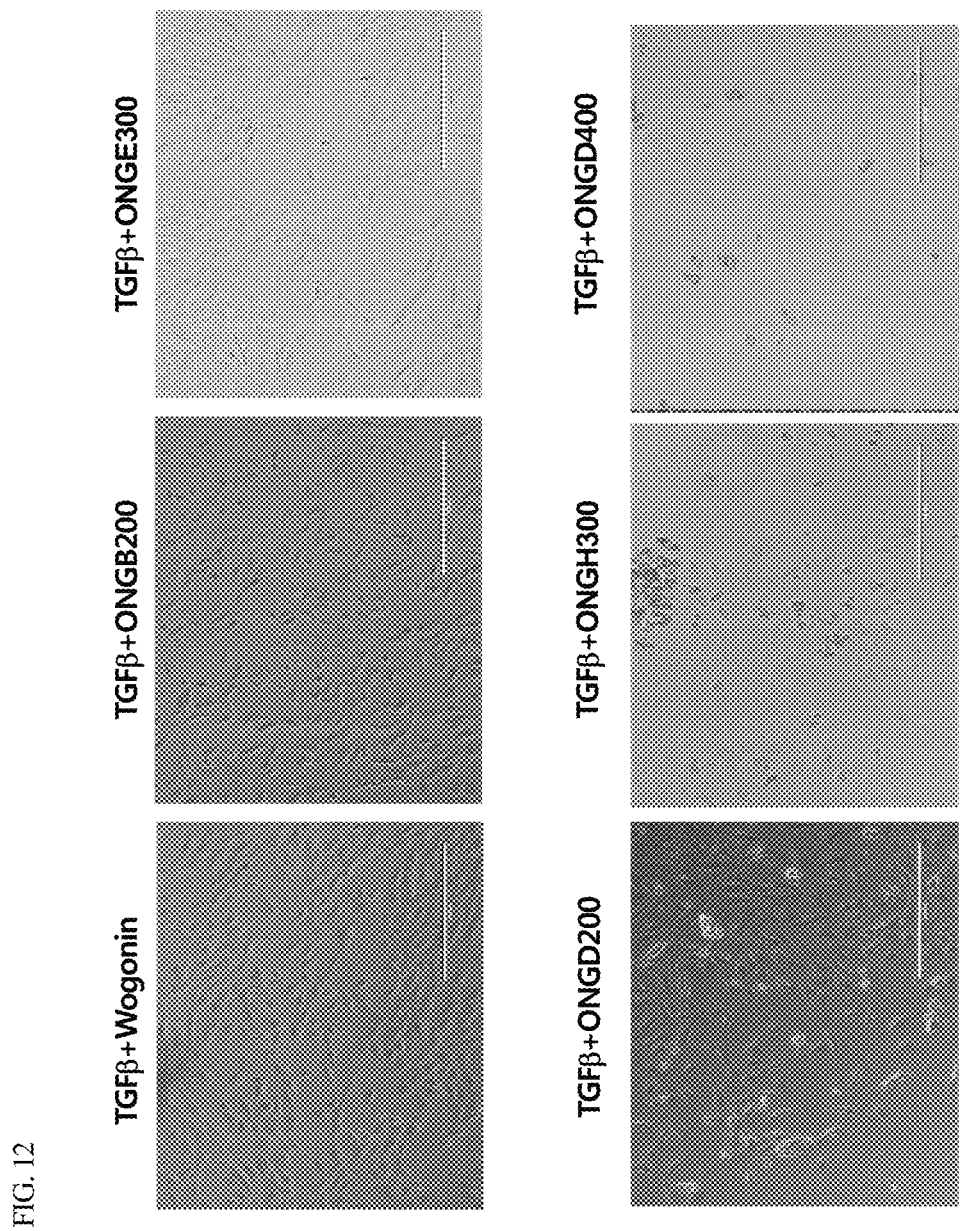

Based on these results, the effect of eupatilin on the treatment of fibrosis has been confirmed and is deemed to be due to the specific structure of eupatilin. Accordingly, compounds having structures similar to the structure of eupatilin are expected to manifest similar effects, and the effects of chromone derivatives other than eupatilin on the treatment of fibrosis were measured in the same manner using ONGHEPA1 cells. Thus, chromone derivatives having structures similar to that of eupatilin, such as those of Chemical Formulas 2, 3, 5 and 7, can be found to exhibit superior fibrosis-inhibiting effects. However, although the chromone derivatives had structures similar to that of eupatilin, the compounds of Chemical Formulas 8, 9 (wogonin), 10, and 11, in which the —O—$R_2$ substituent of Chemical Formula 1 is H, had no effects on the inhibition of fibrosis, and the compounds of Chemical Formula 12, in which the —O—$R_2$ substituent is —OH, and Chemical Formulas 13 and 14, in which the $R_3$ substituent is —O—$CH_3$ (methoxy), exhibited toxicity such as necrosis and the like (FIGS. 11 and 12).

[Chemical Formula 8]

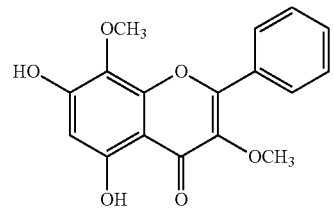

[Chemical Formula 9]

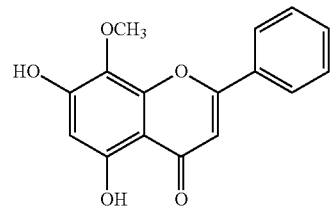

-continued

[Chemical Formula 10]
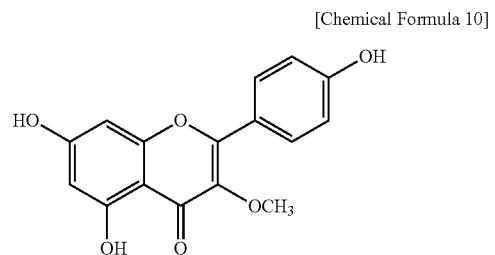

[Chemical Formula 11]
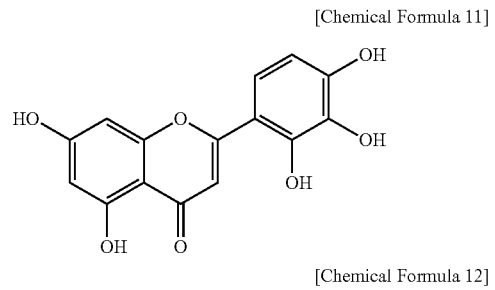

[Chemical Formula 12]
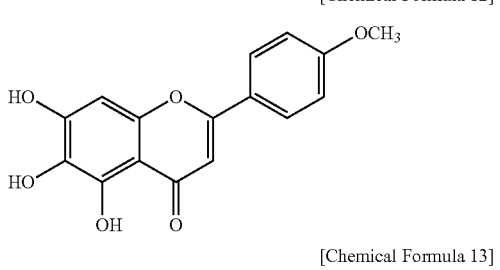

[Chemical Formula 13]
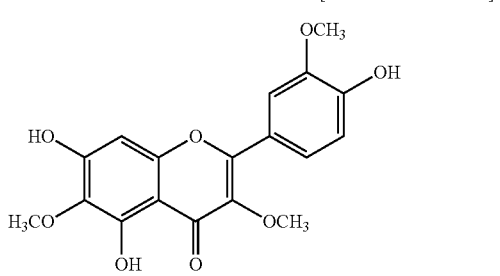

[Chemical Formula 14]
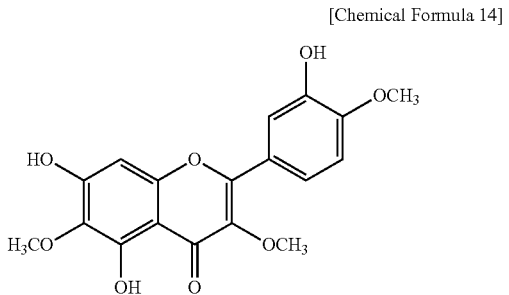

In order to exhibit fibrosis-inhibiting effects, the —O—$R_2$ substituent and the $R_3$ substituent are very important in the structure of Chemical Formula 1. Thus, in the structure of Chemical Formula 1, the case where the —O—$R_2$ substituent is not H or —OH and the $R_3$ substituent is not —O—$CH_3$ is deemed to exhibit the fibrosis-inhibiting effect.

Figure 1:
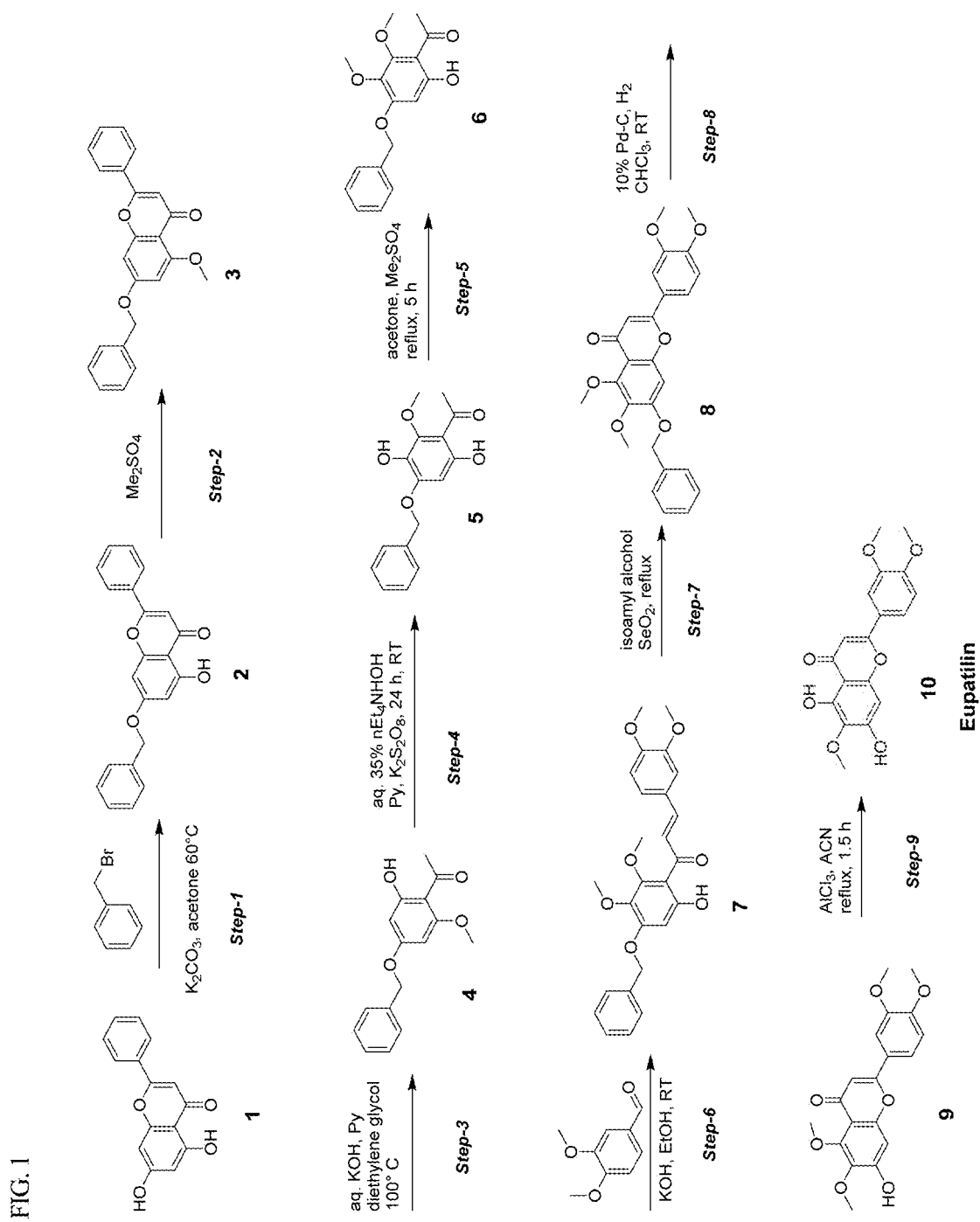
FIG. 1 shows the synthesis of eupatilin, which is one of the chromone derivatives of the present invention.

The chromone derivative of the present invention may be prepared through a typical method, for example, the process of FIG. 1 or modifications thereof, and may be easily purchased from companies that synthesize or sell such compounds.

In the present invention, the pharmaceutical composition may contain the chromone derivative of the invention in an amount of 0.1 to 90 wt % based on the total weight of the composition.

In the present invention, the pharmaceutical composition may be orally or parenterally administered upon clinical administration. Upon parenteral administration, intraperitoneal injection, intrarectal injection, subcutaneous injection, intravenous injection, intramuscular injection, epidural injection in the uterus, intracerebroventricular injection or intrathoracic injection is possible, and the pharmaceutical composition may be used in the form of a typical medical formulation.

In the present invention, the pharmaceutical composition may be used alone or in combination with surgery, radiation therapy, hormone therapy, chemotherapy and biological response modifiers.

The pharmaceutical composition according to the present invention may be administered daily in a dose of about 0.0001 to 100 mg, and preferably 0.001 to 10 mg per kg of body weight based on the chromone derivative contained in the composition, and may be administered once or divided into multiple administrations several times per day, but the dose thereof may vary depending on the patient's body weight, age, gender, state of health, diet, administration time, administration method, excretion rate, and disease severity.

Upon actual clinical administration, a variety of formulations may be parenterally administered. The composition may be formulated using a vehicle or a diluent, such as a filler, an extender, a binder, a humectant, a disintegrant, a surfactant, etc. The formulation for parenteral administration may include a sterile aqueous solution, a non-aqueous solution, a suspension, an emulsion, a lyophilisate, or a suppository. The non-aqueous solution or the suspension may include propylene glycol, polyethylene glycol, a vegetable oil such as olive oil, or an injectable ester such as ethyl oleate. The substrate for the suppository may include Witepsol, Macrogol, Tween 61, cacao oil, laurin oil, glycerogelatin and the like.

The pharmaceutical composition according to the present invention may contain at least one additional active ingredient having the same or similar function, in addition to the chromone derivative of the invention.

A better understanding of the present invention may be obtained via the following examples, which are set forth to illustrate, but are not to be construed as limiting the scope of the present invention.

Chromone Derivative

Used in this embodiment were chromone derivatives, including 2-(3,4-dimethoxyphenyl)-5,7-dihydroxy-6-methoxy-chromone (Chemical Formula 2) (eupatilin), 2-(3,4-dihydroxyphenyl)-5,7-dihydroxy-6-methoxy-chromone (Chemical Formula 3) (hereinafter, referred to as "ONGI300"), 5,7-dihydroxy-2-(4-hydroxyphenyl)-6-methoxy-chromone (Chemical Formula 5) (hereinafter, referred to as "ONGE200"), 5-hydroxy-2-(4-hydroxyphenyl)-6,7-dimethoxy-chromone (Chemical Formula 6) (hereinafter, referred to as "ONGC200"), 2-(3,4-dihydroxyphenyl)-5-hydroxy-6,7-dimethoxy-chromone (Chemical Formula 7) (hereinafter, referred to as "ONGH200"), and wogonin and the like as represented by Chemical Formulas 8 to 14.

Useful in this embodiment, eupatilin, synthesized through the procedures of FIG. 1, was used.

Example 1: Evaluation of Increase in DEC2 Expression

DEC2 is known to be a transcriptional repressor of Twist and Slug, which are EMT regulators. The present inventors have determined that the transcription of EMT regulators such as Twist and Slug was suppressed with an increase in DEC2 expression, and thus tissue fibrosis was inhibited due to the suppression of EMT.

Accordingly, whether DEC2 expression was increased using the chromone derivative of the invention was evaluated. Eupatilin was used as the chromone derivative.

Mouse bone marrow cells (MBMC) were activated with M-CSF (Macrophage-Colony Stimulating Factor) and RANK (Receptor Activator of NFκB) ligand (RANKL) and then incubated for 4 days in the presence of eupatilin at 50 μM, after which the extent of expression of DEC2 was measured.

As illustrated in FIG. 2, eupatilin was confirmed to act as a DEC2 inducer capable of increasing the mRNA expression of DEC2 7- to 8-fold.

Example 2: Evaluation of Effect on Fibrosis of Lung Tissue Induced by Bleomycin The increase in DEC2 expression by eupatilin was confirmed in Example 1, and thus, in order to evaluate the ability of eupatilin to inhibit fibrosis, whether it was possible to practically inhibit tissue fibrosis using eupatilin was checked using actual animal models.

Five-week-old male C57BL/6J mice (weight: 18.2 to 20.5 g) (KOATECH, Korea) were used as experimental animals, and each test group was composed of five experimental animals, as is summarized in Table 1 below.

TABLE 1

| Test group | Bleomycin administration | Eupatilin administration |
|---|---|---|
| Normal control group | — | — |
| Bleomycin-administered group | 40 μg/head | vehicle |
| Bleomycin + 1 μg of eupatilin-administered group | 40 μg/head | 1 μg/20 μL |
| Bleomycin + 5 μg of eupatilin-administered group | 40 μg/head | 5 μg/20 μL |
| Bleomycin + 10 μg of eupatilin-administered group | 40 μg/head | 10 μg/20 μL |
| Bleomycin + 20 μg of eupatilin-administered group | 40 μg/head | 20 μg/20 μL |
| Bleomycin + 40 μg of eupatilin-administered group | 40 μg/head | 40 μg/20 μL |

The experimental animals were bred using a breeding box having a size of 369L×156W×132H (mm) (EU, USA, UK GL compliance) made of a polysulfone material in a SPF (Specific Pathogen Free) and BSL (Bio Safety Level) 2 grade facility. The number of animals in each breeding box was 2 to 3 during the period of quarantine and acclimatization and was also 2 to 3 during the testing period, and the breeding conditions were set to a temperature of 22±2° C., a relative humidity of 50.0±15.0%, a ventilation cycle of 10 to 20 times/hr, a light-dark cycle (a photoperiod) of 12 hr/day (07:00 to 19:00), and an illumination intensity of 150 to 300 Lux.

Pulmonary fibrosis was induced by directly injecting a bleomycin solution into the lungs via the trachea according to the intratracheal instillation (IT) method of Kremer, Laxer and Berkman et al. Specifically, C57BL/6J mice were anesthetized through inhalation with 70% $N_2O$ and 30% $O_2$ gas and 1.5% isoflurane, and the skin of the anterior neck thereof was excised and the organs under the muscle thereof were exposed and then carefully excised using ophthalmic surgical scissors. 50 μL of a bleomycin solution in distilled water was directly injected into the lungs all at once via the excised organ using a 1 mL syringe fitted with a 19-gauge injection needle having a blunt tip. Immediately after the injection, the excised skin of the anterior neck was sutured and the mice were allowed to recover from the anesthetic, transferred into a general breeding cage and then bred. The administration of bleomycin was performed using a visual instillobot, and bleomycin-HCl 40 μg/50 μL was administered once and a pulmonary fibrosis induction period of 12 days was set.

Eupatilin was used by being dissolved in a DPBS buffer (containing 1% DMSO), and the amount of eupatilin that was administered was 1 mL/kg, and the dose for each individual was calculated based on the recent body weight thereof 12 days after the administration of bleomycin, eupatilin was forcibly nasally administered once a day (5 times a week) for 1 week using a micropipette. For 2 to 3 days after the administration of eupatilin, toxic symptoms and the occurrence of death were observed, but no particularly abnormal symptoms were observed after the administration of bleomycin and eupatilin.

Three mice per test group were selected and the lung tissues thereof were separated. The separated lung tissues were stained with Masson's trichrome and observed with a microscope. As the result thereof, pulmonary fibrosis was induced by the addition of bleomycin, and was confirmed to be inhibited due to the administration of eupatilin in the group administered with 20 μg of eupatilin and the group administered with 40 μg of eupatilin. In particular, pulmonary fibrosis was more effectively inhibited in the group administered with 40 μg of eupatilin (FIG. 3).

Consequently, eupatilin can be found to be useful as an effective therapeutic agent for a fibrotic disease, especially pulmonary fibrosis.

Example 3. Evaluation of Effect on Liver Fibrosis

In order to evaluate the effect of the chromone derivative on liver fibrosis, HSC was prepared and then treated with TGF-β, and during the induction of liver fibrosis, the effect of the chromone derivative was measured.

3-1. Preparation of HSC

The liver tissue was separated from C57BL/6 mice and a single-cell suspension thereof was made, and immortalized cells were obtained through continuous culture and were confirmed to be mesenchymal stem cells (MSC) of HSC via RT-PCR (Reverse Transcription Polymerase Chain Reaction) using MC (Immunohistochemistry) and FACS (Fluorescence-Activated Cell Sorting). This cell line was called "ONGHEPA1", and was deposited with the Korean Collection for Type Cultures (KCTC) of the Korea Research Institute of Bioscience and Biotechnology and assigned accession number KCTC13086BP.

HSC is closely related with liver fibrosis. HSC was converted into myofibroblasts, and various proteins associated with EMT (Epithelial Mesenchymal Transition) were secreted, thereby inducing liver fibrosis. Thus, the mesenchymal stem cells of HSC may be used as an excellent liver fibrosis model.

RT-PCR result: Albumin negative result, from which the ONGHEPA1 cell line was confirmed not to be hepatocytes. For reference, HSC was not hepatocytes, and thus did not express albumin.

IHC result: the ONGHEPA1 cell line was immobilized and then subjected to IHC using the anti-GATA4 and anti-CK-18 antibodies, thereby expressing GATA4 and CK-18, that is, endo/ectodermal markers. This means that the ONGHEPA1 cell line is not hepatocytes (FIG. 4).

FACS result: To check whether the ONGHEPA1 cell line is MSC of the liver, FACS was performed with the MSC marker antibody. CD29, CD44, CD71 and CD106 were expressed on the surface of cells, and thus ONGHEPA1 was confirmed to be MSC (FIG. 5).

3-2. Analysis of Fibrotic Characteristics of Liver Fibrosis Cell Line

The most important cells that cause liver fibrosis are HSC. HSC differentiates into various cells, one of which is myofibroblasts. Also, HSC secretes a large amount of extracellular matrix protein (ECM) between the cells to thus slow the movement of the cells. Collagen α1 is the most abundant ECM protein. Simultaneously, α-SM-actinin (alpha smooth muscle actinin) is over-expressed in the fibroblasts, thus hardening the cytoskeleton.

Using such properties of HSC, the fibrotic characteristics of ONGHEPA1 were measured. To induce fibrosis, TGF-β (transforming growth factor beta) was added, and the morphologies of the cells were observed after 6 hr, 12 hr, 24 hr, and 48 hr. Consequently, fibrosis was confirmed to progress considerably after 24 hr and further progress after 48 hr (A of FIG. 6).

3-3. Analysis of Effect of Eupatilin

Based on the fibrotic characteristics of ONGHEPA1 cells as confirmed in 3-2 above, the test for analyzing the effect of eupatilin was performed.

While ONGHEPA1 cells were incubated, they were treated with TGF-β to induce fibrosis, and 50 μM of eupatilin was added to the culture medium. Unlike the TGF-β-treated fibrosis test group (Example 3-2, A of FIG. 6), the differentiation of HSC into myofibroblasts and also fibrosis were not observed after 24 hr (B of FIG. 6). Such results show that eupatilin was capable of effectively blocking the differentiation of MSC-derived HSC into myofibroblasts, which is regarded as a major cause of liver fibrosis.

In order to more clearly evaluate the effect of eupatilin as above, changes were measured when ONGHEPA1 cells were first treated with eupatilin, washed to remove eupatilin and then treated with TGF-β to induce fibrosis. As shown in FIG. 7, even when the cells were pretreated with eupatilin, the progress of fibrosis was not inhibited in the absence of eupatilin during the course of fibrosis. This means that eupatilin is directly associated with the course of fibrosis to thus inhibit the progress of fibrosis.

On the contrary, changes were measured when ONGHEPA1 cells were first treated with TGF-β to induce fibrosis, washed to remove TGF-β and then treated with eupatilin. As shown in FIG. 8, normal cells such as a control group were maintained because of the treatment with eupatilin despite the induction of fibrosis due to pretreatment with TGF-β. Even when fibrosis was already progressed, eupatilin was able to restore the cells to their original normal condition.

In order to more clearly evaluate whether eupatilin was able to restore the cells that already undergone fibrosis to normal cells, changes were measured when ONGHEPA1 cells were treated with TGF-β for 24 hr to induce complete fibrosis and then treated with eupatilin. As shown in FIG. 9, eupatilin can be concluded to restore the cells in which fibrosis has been completely induced by TGF-β to their normal condition. This means that fibrosis that has progressed considerably can be effectively treated using eupatilin.

Also in order to evaluate whether the effect of eupatilin described above is due to the influence of eupatilin on EMT, for the cells incubated for 24 hr in each test group, the extent of expression of ECM, for example, Col1 (type 1 Collagen), Vim (Vimentin) and Twist, was measured through real-time RT-PCR. As illustrated in FIG. 10, fibrosis was induced by the addition of TGF-β, and thus the expression of EMT regulators was increased, but the expression thereof was inhibited by the addition of eupatilin.

Therefore, eupatilin can be concluded to be useful as an effective therapeutic agent for a fibrotic disease, especially liver fibrosis.

3-4. Analysis of Effects of Chromone Derivatives Other than Eupatilin

The effects of various chromone derivatives other than eupatilin on fibrosis were measured in the same manner as in Example 3-3. While ONGHEPA1 cells were incubated, fibrosis was induced by TGF-β, and a chromone derivative was added at a concentration of 50 μM to the culture medium.

As shown in FIG. 11, the chromone derivatives such as ONGI300, ONGC200, ONGE200 and ONGH200 were effective at inhibiting the progress of fibrosis. Meanwhile, as shown in FIGS. 11 and 12, wogonin, ONGA100, ONGB200 and ONGE300 had no effects or very low effects of inhibiting the progress of fibrosis, and ONGD200, ONGH300 and ONGD400 caused toxicity such as necrosis, etc.

Example 4. Global Gene Expression Analysis

For a mechanism for the therapeutic effect on fibrosis, the global gene expression of DMSO-treated ONGHEPA1 cells (a control group), ONGHEPA1 cells in which fibrosis was induced by TGF-β, and ONGHEPA1 cells treated with TGF-β and eupatilin was measured.

The cells were treated with DMSO, TGF-β or eupatilin for 24 hr, and total RNA was isolated to manufacture a library, after which about 10,000 expressed mRNA species in a total transcriptome of 30 Gb were analyzed using an Illumina High-seq sequencer.

The following results were obtained (FIG. 13).

1) The number of genes expressed in common in three test groups: 9,033

2) The number of genes specifically expressed in a control group ONGHEPA1 cell line: 628

3) The number of genes specifically expressed upon treatment with TGF-β: 169

4) The number of genes specifically expressed upon treatment with TGF-β and eupatilin: 150

5) The number of genes expressed in common in a TGF-β-treated group and a TGF-β+eupatilin-treated group: 657

6) The number of genes expressed in common in a control group and a TGF-β-treated group: 171

7) The number of genes expressed in common in a control group and a TGF-β+eupatilin-treated group: 188

When the ONGHEPA1 cell line was treated with TGF-β, the expression of 826 (=169+657) genes was induced and thus an EMT program was activated. Thereafter, additional treatment with eupatilin caused the expression of 338 (=150+188) genes to be further induced to thereby reverse the EMT program to its original state, resulting in transdifferentiation.

The results of a comparison of the p-value and the induction fold of genes whose expression was changed in a TGF-β-treated group and a TGF-β+eupatilin-treated group are depicted in the form of a volcano plot in FIG. 14.

EMT, which is a cellular program implicated in the generation of tumors, differentiation of stem cells and fibrosis, is known to be associated with hundreds of genes to date. Collagen α1, Vimentin, α-SM-actinin, Twist, Snail1, Snail2 (=Slug), N-Cadherin and the like are representative EMT markers. In this Example, eupatilin was revealed to inhibit the expression of Collagen α1, Vimentin and Twist genes due to TGF-β, and, based on the results of RNA-Seq, 976 genes were newly expressed by the treatment with TGF-β or eupatilin, and the expression of 9,033 genes found in common in all treatment groups was slightly increased or decreased. Hence, all of them are regarded as directly or indirectly affecting EMT. Accordingly, all of about 10,000 genes, the expression of which is adjusted to the statistical level of $p<0.05$ through treatment with TGF-β and eupatilin, were selected, a big data-based gene interactome, encompassing all functions of proteins encoded by the selected genes, was analyzed in an unbiased manner, and the network therebetween was assayed (FIG. 15).

Surprisingly, eight gene network hubs were used to form a single network framework by means of different nodes, and eight hubs were mainly composed of EMT-associated genes. A cytoskeleton proteome hub (I) and a collagen proteome hub (II) were configured to form a network by means of an integrin α1 (Itga1) node, and a cell cycle proteome hub-1 (III) including Cyclin B1, which is known to be an important factor of EMT, was connected to a protein kinase C alpha (PKCA) node to thus construct a rigid network by means of an integrin beta 3 (Itbg3) node together with the above three proteome hubs. The other second cell cycle hub-2 (IV) was configured such that a transcriptional factor Lymphoid Enhancer Binding Factor 1 (Lef1) node was connected by means of Cyclin D1 (Ccdn1) and the Adenylate Cyclase 9 (Adcy9) signal transmission hub was networked with EMT factors, such as C-Fos, CCL2 and Junb, by means of Chemokine CXCL16, which is important for EMT. Here, the Adcy9 signal transmission hub is deemed to be a new EMT regulator that is affected by eupatilin. A CD44 hub (V), which is known to significantly affect EMT of cancer cells, was connected to a secreted phosphoprotein 1 (Spp1/Osteopontin) node, which is associated with cell migration and invasion. Also, Spp1 (osteopontin) was known to be an important EMT factor. The Spp1 node was networked with ECM protease, that is, Mmp3. The hub (VI) including Fibrillin and Elastin, which are important proteins of an ECM and are main EMT factors, was connected to the central node, namely integrin b3 (Itgb3). The EMT-causing cytokine-transforming growth factor b2 proteome hub (VII) was configured to include serpine1 and Figf (=VegfD) and to construct a network with the kinase insert domain receptor (Kdr) node. Known as an important receptor of EMT, the semaphorin and cholesterol receptor (Vldr) hub (VIII) was configured to include plexin D, semaphorin 3E, neurophilin and NGF and the semaphorin receptor hub was configured to form a network with the Kdr node. The Vldr receptor hub was connected to the insulin receptor substrate 21 (rs2) via the nerve growth factor (Ngf) to form a signal transmission axis. As the main transcriptional factor of EMT, a Snail2 (=Slug)–E-Cadherin (=Cadh1) node was configured to construct a network with the cell cycle proteome hub (II), and E-Cadherin was connected to the important EMT factors, for example, Mmp3, caveolin (Cav), Tenascin C (Tnc) and PKCa. PKCa was configured to construct a network with the cytoskeleton and collagen proteome hubs by means of integrin b4. Tenascin C was directly connected to the integrin b3.

<Hub I. Cytoskeleton Proteome Hub>

Troponin I1 & Troponin I2, Tropomyosin 2, Transgelin, α2 smooth muscle actin, Myosin heavy chain 9 & 11, Leiomodin 1, γ2 smooth muscle actinin, Laminin subunit α4

<Hub II. Collagen Proteome Hub>

Collagen 4 α5 & α6, Collagen 5 α1 & α3, Collagen 6 α3, Collagen 8 α1 & α5, Collagen 11 α1, Collagen 12 α1, Collagen 15 α1

<Hub III. Cell Cycle Proteome Hub-1>

Cyclin B1, Gadd45a, Cyclin F, ASPM, NIMA-related kinase (Nek2), Optineurin

<Hub IV. Cell Cycle Proteome Hub-2>

Cyclin D1, Cdk14, C-Fos, Junb, CCL2, CCL7

<Hub V. CD44-Associated Proteome Hub>

Cd44, Hypoxia Up-Regulated 1 (Hyou1), Ncam, Calreticulin, Immunity-Related GTPase M (Irgm1), Parp4, Parp9, Pdia4 & Pdia6

<Hub VI. Fibrillin Proteome Hub>

Efemp2 (EGF Containing Fibulin-Like Extracellular Matrix Protein 2), Fibrillin 5 (FbnS), Fibrillin 2 (Fbn2), Elastin (Eln), Fibrillin 1 (Fbn1)

<Hub VII. Transforming Growth Factor Beta 2 Proteome Hub>

RAR Related Orphan Receptor A (Rora), Neuronal PAS Domain Protein 2 (Npas2), Serpine 1, Transforming Growth Factor Beta 2 (Tgfb2), Vascular Endothelial Growth Factor D (Figf)

<Hub VIII. Semaphorin & Vldr Receptor Proteome Hub>

Plexin D1, Semaphorin 3E, Semaphorin 3A, Neurophilin 1, Very Low Density Lipoprotein Receptor, Nerve Growth Factor (Ngf)

<Major Network Node of TGF-β-Eupatilin Interactome>

Integrin α1, Integrin β3, Integnn β4, Protein kinase Cα, Len, Slug, Cadherin1 (=E-Cadherin), Adenylate cyclase 9, Spp1 Osteopontin), Fibrilin1, Dedicator of cytokinesis 1 (Dock1), Syk2, Notch4, etc.

Therefore, eupatilin acted to reverse the EMT program that was induced by the treatment with TGF-β. This mechanism was composed of the birth and death of eight EMT proteome hubs, that is, cytoskeleton proteome hub (I), collagen proteome hub (II), cell cycle proteome hub-1 (III), cell cycle proteome hub-2 (IV), CD44-associated proteome hub (V), fibrillin proteome hub (VI), TGF-β2 proteome hub (VII), and Semaphorin and Vldr receptor proteome hub (VIII), and integrin α1, integrin β3, protein kinase Cα, Snali2, Kdr, E-cadherin, and adenylate cyclase 9 are nodes that are important for connecting the network.

Example 5. Analysis of Target Gene

Based on the analytical results of the global gene expression as in Example 4, among genes that deteriorate expression upon treatment with eupatilin after the addition of ONGHEPA1 cells with TGF-β to induce expression, specifically among genes that cause a difference in expression between a TGF-β-treated group and a eupatilin-treated group, genes in which expression was greatly increased by the addition of TGF-β but seldom occurred upon the addition of eupatilin were screened.

Accordingly, 103 genes thus screened are shown in Tables 2 to 5 below.

TABLE 2

| No. | Description (Abbreviation) | Log2fc | p-value |
|---|---|---|---|
| 1 | Actin, gamma2 (Actg2) | −5.83 | 0.00005 |
| 2 | Periostin (Postn) | −4.92 | 0.00005 |
| 3 | Collagen, type XI, alpha 1 (Col11a1) | −3.11 | 0.00005 |
| 4 | Fibronectin 1 (Fn1) | infinite | 0.0002 |
| 5 | Thrombospondin, type I domain containing 7A (Thsd7a) | 5.06 | 0.0002 |
| 6 | TraB domain containing 2B (Trabd2b) | 2.75 | 0.0003 |
| 7 | Collagen type XV, alpha 1 (Col5a1) | 2.26 | 0.00055 |
| 8 | Slit homolog 3 (Slit3) | 3.65 | 0.00065 |
| 9 | Cell migration inducing protein, hyaluronan binding (Cemip) | −2.75 | 0.00095 |
| 10 | Inhibition beta-A (Inhba) | 2.19 | 0.0015 |
| 11 | Spectrin alpha, erythrocytic 1 (Spta1) | 4.01 | 0.00165 |
| 12 | Exocyst complex component 4 (Exoc4) | 2.9 | 0.0019 |
| 13 | A disintegrin-like and metallopeptidase with thrombospondin type 1 motif 12 (Adamts12) | 2.09 | 0.0025 |
| 14 | Ephrin B2 (Efnb2) | 1.92 | 0.0038 |
| 15 | c-fos induced growth factor (Figf) | 2.49 | 0.0044 |
| 16 | Elastin (Eln) | 3.28 | 0.00555 |
| 17 | Heparan sulfate 6-O-sulfotransferase 2 (Hs6st2) | 3.26 | 0.0056 |
| 18 | Perlecan (Heparan sulfate proteoglycan2) (Hspg2) | infinite | 0.0057 |
| 19 | Tubulin-specific chaperone d (Tbcd) | 2.11 | 0.00595 |
| 20 | Natriuretic peptide receptor 3 (Npr3) | 2.82 | 0.00675 |
| 21 | Serin (or cysteine) peptidase inhibitor, clade F, member 1 (Serpinf1) | 1.99 | 0.00685 |
| 22 | TLC domain-containing protein 2 (Tlcd2) | infinite | 0.0074 |
| 23 | Fras 1 related extracellular matrix protein 1 (Frem1) | 2.36 | 0.0075 |
| 24 | Caldesmon 1 (Cald1) | infinite | 0.0074 |
| 25 | Lysyl oxidase-like 2 (Loxl2) | 1.93 | 0.0078 |
| 26 | Tissue inhibitor of metalloproteinase 3 (Timp3) | infinite | 0.00785 |
| 27 | Collagen, type III, alpha 1 (Col3a1) | infinite | 0.0083 |
| 28 | Protein disulfide isomerase associated 6 (Pdia6) | 1.85 | 0.00835 |
| 29 | Pleiotrophin (Ptn) | 2.06 | 0.00875 |
| 30 | Prostate androgen-regulated mucin-like protein 1 (Parm1) | 1.57 | 0.01225 |

TABLE 3

| No. | Description (Abbreviation) | Log2fc | p-value |
|---|---|---|---|
| 31 | Dihydropyrimidinase-like 3 (Dpysl3) | infinite | 0.0138 |
| 32 | Collagen, type XII, alpha 1 (Col12a1) | 2.02 | 0.01435 |
| 33 | Crystallin, zeta (quinone reductase)-like 1 (Cryzl1) | infinite | 0.01475 |
| 34 | Calumenin (Calu) | infinite | 0.015 |
| 35 | Follistatin-like 1 (Fstl1) | infinite | 0.0156 |
| 36 | Vinculin (Vcl) | infinite | 0.01575 |
| 37 | Cyclin D2 (Ccnd2) | 2.29 | 0.01585 |
| 38 | A disintegrin-like and metallopeptidase (reprolysin type) with thrombospondin type 1 motif 2 (Adamts2) | 2.08 | 0.1685 |
| 39 | Dysferlin (Dysf) | 2.06 | 0.01765 |
| 40 | Olfactomedin 2 (Olfm2) | 1.9 | 0.01845 |
| 41 | Ubiquitin-like modifier activating enzyme 1 (Uba1) | infinite | 0.01855 |
| 42 | Leprecan 1 (Lepre1) | 1.75 | 0.01865 |
| 43 | Prosaposin (Psap) | infinite | 0.01875 |
| 44 | Latent transforming growth factor beta binding protein 1 (Ltbp1) | 3.32 | 0.01985 |
| 45 | Spectrin beta, non-erythrocytic 1 (Sptbn1) | infinite | 0.02 |
| 46 | Palladin, cytoskeletal associated protein (Palld) | infinite | 0.02005 |
| 47 | Protein FAM 53B (Fam53b) | infinite | 0.02015 |
| 48 | Caveolin 1, Caveolae protein (Cav1) | 1.76 | 0.02025 |
| 49 | Nischarin (Nisch) | infinite | 0.02075 |
| 50 | Fibronectin type III domain containing 1 (Fndc1) | 1.75 | 0.02105 |
| 51 | Tropomyosin 1, alpha (Tpm1) | infinite | 0.02145 |
| 52 | Doublecortin-like kinase 1 (Dclk1) | 1.54 | 0.023 |
| 53 | Actin alpha 4 (Actn4) | infinite | 0.0241 |
| 54 | Colony stimulating factor 1 (macrophage) (Csf1) | 2.15 | 0.02535 |
| 55 | Tenascin C (Tnc) | 5.1 | 0.02575 |
| 56 | Intersectin 1 (SH3 domain protein 1A) (Itsn1) | infinite | 0.0263 |
| 57 | Transforming, acidic coiled-coil containing protein 2 (Tacc2) | infinite | 0.0267 |
| 58 | Pleckstrin and sec7 domain containing 3 (Psd3) | 1.43 | 0.0275 |
| 59 | C-terminal-binding protein 2 (Ctbp2) | infinite | 0.0277 |
| 60 | Heat shock protein 90, alpha (cytosolic), class A member 1(Hsp90aa1) | infinite | 0.029 |

TABLE 4

| No. | Description (Abbreviation) | Log2fc | p-value |
|---|---|---|---|
| 61 | Septin2 (Sept2) | infinite | 0.02975 |
| 62 | Epidermal growth factor-containing fibulin-like extracellular matrix protein 2 (Efemp2) | 1.66 | 0.03005 |
| 63 | EH-domain containing 2 (Ehd2) | infinite | 0.03025 |
| 64 | Coatomer protein complex, subunit gamma 1 (Copg1) | infinite | 0.03045 |
| 65 | v-myc myelocytomatosis viral related oncogene, neuroblastoma derived (Mycn) | 2.05 | 0.031 |
| 66 | Lethal giant larvae homolog 1 (Ligi1) | infinite | 0.0331 |
| 67 | Interleukin 18 receptor accessory protein (Il18rap) | 1.69 | 0.0332 |
| 68 | Willians-Beuren syndrome chromosome region 17 homolog (Wbscr17) | −2.83 | 0.03325 |
| 69 | Collagen type 1 alpha 1 (Col1a1) | −1.64 | 0.0334 |
| 70 | Synaptopodin (Synpo) | −infinite | 0.03375 |
| 71 | Integral beta 5 (Itgb5) | −infinite | 0.0342 |
| 72 | Tankyrase, TRF1-interacting ankyrin-related ADP-ribose polymerase 2 (Tnks2) | −infinite | 0.0349 |
| 73 | Procollagen-lysine, 2-oxoglutarate 5-dioxygenase 3 (Plod3) | −2.01 | 0.0355 |
| 74 | BTAF1 RNA polymerase II, B-TFIID transcription factor-associated (Btaf1) | −infinite | 0.0356 |
| 75 | Dynein cytoplasmic 1 heavy chain 1 (Dync1h1) | −infinite | 0.03565 |
| 76 | Aurora kinase A (Aurka) | −15.3 | 0.03595 |
| 77 | WNK lysine deficient protein kinase 1 (Wnk1) | −infinite | 0.03685 |
| 78 | Collagen type VII alpha1 (Col7a1) | −15.2 | 0.03715 |
| 79 | Procollagen-proline, 2-oxoglutarate 4-dioxygenase (proline 4-hydroxylase), alpha 1 polypeptide (P4ha1) | −1.81 | 0.0375 |
| 80 | Spectrin repeat containing nuclear envelope 2 (Syne2) | −infinite | 0.0376 |
| 81 | Cell cycle associated protein 1 (Caprin1) | −infinite | 0.0382 |
| 82 | Calreticulin (Calr) | −1.74 | 0.03845 |
| 83 | Endoglin (Eng) | −infinite | 0.03895 |
| 84 | Microtubule-associated protein 4 (Map4) | −infinite | 0.039 |
| 85 | rho/rac guanine nucleotide exchange factor (GEF) 2 (Arhgef2) | −infinite | 0.03915 |
| 86 | Inositol hexakisphosphate kinase 1 (Ip6k1) | −infinite | 0.03985 |
| 87 | TEA Domain Transcription factor 1 (TEAD1) | −infinite | 0.04005 |
| 88 | Procollagen lysine, 2-oxoglutarate 5-dioxygenase 2 (Plod2) | −1.48 | 0.0402 |
| 89 | Family with sequence similarity 175, member B (Fam175b) | −infinite | 0.0413 |
| 90 | ArfGAP with SH3 domain, ankyrin repeat and PH domain 1 (Asap1) | −infinite | 0.0414 |

TABLE 5

| No. | Description (Abbreviation) | Log2fc | p-value |
|---|---|---|---|
| 91 | Laminin, alpha 4 (Lama4) | −1.29 | 0.04145 |
| 92 | Serine (or cysteine) peptidase inhibitor, clade E, member 1 (Serpine 1) | −1.78 | 0.0419 |

TABLE 5-continued

| No. | Description (Abbreviation) | Log2fc | p-value |
|---|---|---|---|
| 93 | Importin-4 (Ipo4) | −infinite | 0.04235 |
| 94 | Transformation/transcription domain-associated protein (Trrap) | −infinite | 0.043 |
| 95 | Surfeit 1 (SURF1) | −infinite | 0.044 |
| 96 | Oxysterol binding protein-like 9 (Osbpl9) | −infinite | 0.0458 |
| 97 | Endoplasmic reticulum-golgi intermediate compartment 1 (ERGIC1) | −1.26 | 0.0465 |
| 98 | Ring finger protein 145 (Rnf145) | −infinite | 0.04665 |
| 99 | AXL receptor tyrosine kinase (Axl) | −infinite | 0.048 |
| 100 | Latent transforming growth factor beta binding protein 2 (Ltbp2) | −infinite | 0.04845 |
| 101 | Latent transforming growth factor beta binding protein 4 (Ltbp4) | −infinite | 0.0492 |
| 102 | Multiple coagulation factor deficiency 2 (Mcfd2) | −1.28 | 0.04935 |
| 103 | Thymoma viral proto-oncogene 1 (Akt1) | −infinite | 0.04985 |

Based on the results of measurement of functions and related research of 103 genes, most of them were identified as factors associated with EMT. Particularly, there is a research report that pulmonary fibrosis was hardly observed in the case where Follistatin-like 1 (Fstl1) gene was knocked out, even when pulmonary fibrosis was induced by bleomycin (Dong et al., 2015).

ACCESSION NUMBER

Depositary Institution: Korea Research Institute of Bioscience and Biotechnology
Accession Number: KCTC13086BP
Accession Date: 20160825

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of treating a disease caused by fibrosis of an organ or tissue in vivo in a subject in need thereof, comprising:
providing a pharmaceutical composition comprising 2-(3,4-dimethoxyphenyl)-5,7-dihydroxy-6-methoxy-chromone or a pharmaceutically acceptable salt thereof, as an active ingredient; and
administering the pharmaceutical composition to the subject, wherein the disease is treated,
wherein the disease is selected from the group consisting of idiopathic pulmonary fibrosis, myelofibrosis, and kidney fibrosis.

* * * * *